(12) United States Patent
Dayicioglu et al.

(10) Patent No.: US 10,322,034 B1
(45) Date of Patent: Jun. 18, 2019

(54) HYDROCOLLOID DRESSING FOR PRECISE NIPPLE POSITIONING AFTER NIPPLE- OR SKIN-SPARING MASTECTOMY

(71) Applicants: Deniz Dayicioglu, Tampa, FL (US); Rose Theresa Tillis, Tampa, FL (US)

(72) Inventors: Deniz Dayicioglu, Tampa, FL (US); Rose Theresa Tillis, Tampa, FL (US)

(73) Assignee: University of South Florida, Tampa, FL (US)

( * ) Notice: Subject to any disclaimer, the term of this patent is extended or adjusted under 35 U.S.C. 154(b) by 532 days.

(21) Appl. No.: 15/255,993

(22) Filed: Sep. 2, 2016

Related U.S. Application Data

(60) Provisional application No. 62/214,344, filed on Sep. 4, 2015.

(51) Int. Cl.
*A61F 13/00* (2006.01)
*A61F 13/14* (2006.01)
*A61F 13/02* (2006.01)

(52) U.S. Cl.
CPC ........ *A61F 13/145* (2013.01); *A61F 13/0253* (2013.01); *A61F 2013/00272* (2013.01); *A61F 2013/00289* (2013.01)

(58) Field of Classification Search
CPC .......................... A61B 5/02055; A61B 5/021; A61B 5/04085; A61B 5/04087; A61B 5/04325;

(Continued)

(56) References Cited

U.S. PATENT DOCUMENTS 4,759,354 A   7/1988   Quarfoot
5,681,579 A   10/1997  Freeman
(Continued)

FOREIGN PATENT DOCUMENTS

CN   101862470   10/2010
CN   102302798   1/2012
(Continued)

OTHER PUBLICATIONS

Slavin et al. Skin-Sparing Mastectomy and Immediate Reconstruction: Oncologic Risks and Aesthetic Results in Patients with Early-Stage Breast Cancer. Plastic and Reconstructive Surgery. 1998; vol. 102, No. 1, pp. 49-62. (Year: 1998).*
(Continued)

*Primary Examiner* — Kim M Lewis
(74) *Attorney, Agent, or Firm* — Michele L. Lawson; Nilay J. Choksi; Smith & Hopen, P.A.

(57) ABSTRACT

An apparatus and method/technique that uses a hydrocolloid dressing that results in both improved circulation and aesthetic success with optimal nipple positioning. By applying a specific pattern of the adhesive hydrocolloid dressing to the mastectomy flaps, stability of the nipple-areolar complex (NAC) in the desired higher position could be achieved. In operation, the hydrocolloid dressing is placed over the breast after surgery (while also leaving the incision site uncovered), and remains in place for a suitable amount of time. The hydrocolloid dressing can be applied on either side or both sides of the nipple during expansion phase to precisely control nipple position. Different designs of the hydrocolloid dressing are contemplated herein.

13 Claims, 26 Drawing Sheets

(58) Field of Classification Search

CPC .............. A61B 5/1118; A61B 5/14532; A61B 5/14551; A61B 5/0816; A61B 5/087; A61B 5/0006; A61B 5/0022; A61B 5/03; A61B 5/0452; A61B 5/14542; A61B 5/6823; A61B 5/7455; A61B 17/32053; A61B 2017/00761; A61B 2018/1807; A61B 5/0071; A61B 5/01; A61B 5/04017; A61B 5/1117; A61B 5/445; A61B 10/00; A61B 17/205; A61B 17/3417; A61B 18/18; A61B 2017/00747; A61B 2017/00792; A61B 2017/00796; A61B 2017/3454; A61B 2018/00452; A61B 2217/005; A61B 2505/07; A61B 2560/0214; A61B 2560/0271; A61B 2560/0415; A61B 2560/045; A61B 2562/0219; A61B 2562/164; A61B 5/0042; A61B 5/0059; A61B 5/1116; A61B 5/4519; A61B 5/6833; A61B 5/72; A61B 5/7405; A61B 5/742; A61B 5/7475; A61B 10/0233; A61B 10/0266; A61B 10/0283; A61B 17/32002; A61B 17/3203; A61B 17/3205; A61B 17/32093; A61B 17/3213; A61B 17/3478; A61B 17/545; A61B 18/14; A61B 18/203; A61B 2010/0225; A61B 2017/0023; A61B 2017/00402; A61B 2017/00424; A61B 2017/00473; A61B 2017/00544; A61B 2017/00734; A61B 2017/00752; A61B 2017/00756; A61B 2017/00769; A61B 2017/320004; A61B 2017/320064; A61B 2017/32035; A61B 2017/3437; A61B 2562/06; A61B 2562/166; A61B 50/13; A61B 5/0077; A61B 5/0245; A61B 5/04525; A61B 5/0456; A61B 5/0468; A61B 5/091; A61B 5/14552; A61B 5/150022; A61B 5/150099; A61B 5/150236; A61B 5/150244; A61B 5/150305; A61B 5/150343; A61B 5/150427; A61B 5/150442; A61B 5/150503; A61B 5/150969; A61B 5/150984; A61B 5/15113; A61B 5/15117; A61B 5/1513; A61B 5/15142; A61B 5/4809; A61B 5/4818; A61B 5/6801; A61B 5/6832; A61B 5/7282; A61B 7/003; A61B 90/02

See application file for complete search history.

(56) References Cited

U.S. PATENT DOCUMENTS

| 6,201,164 | B1 | 3/2001 | Wulff et al. |
| 6,235,964 | B1 | 5/2001 | Kadash et al. |
| 6,861,067 | B2 | 3/2005 | McGhee et al. |
| 2007/0233273 | A1 | 10/2007 | Connell |
| 2012/0123535 | A1 | 5/2012 | Alejandro |
| 2012/0185041 | A1 | 7/2012 | Mortarino et al. |
| 2013/0304098 | A1 | 11/2013 | Mortarino |

FOREIGN PATENT DOCUMENTS

| EP | 0340945 | 11/1989 |
| EP | 1020195 | 7/2000 |
| WO | 2006050091 | 5/2006 |
| WO | 2014164769 | 10/2014 |

OTHER PUBLICATIONS

Dayicioglu et al. Duoderm-Bra for Nipple-Sparring Mastectomy. Annals of Plastic Surgery. Jun. 2016; vol. 76, Supplement 4, pp. S280-S285. (Year: 2016).*

Komorowski, A. L., et al. Necrotic Complications after Nipple- and Areola-Sparing Mastectomy. World Journal of Surgery, Jul. 21, 2006; 30:1410-1413.

Salzberg, C. A. Focus on Technique: One-Stage Implant-Based Breast Reconstruction. Plastic and Reconstructive Surgery Journal. 2012; 130:95S-103S.

Austad, E. D., et al. Histomorphologic Evaluation of Guinea Pig Skin and Soft Tissue after Controlled Tissue Expansion. Plastic and Reconstructive Surgery. Dec. 1982; 70:704-710.

Antony, A. K., et al. Acellular Human Dermis Implantation in 153 Immediate Two-Stage Tissue Expander Breast Reconstructions: Determining the Incidence and Significant Predictors of Complications. Plastic and Reconstructive Surgery. 2010; 125:1606-1614.

Park, S. W., et al. Managing necrosis of the nipple-areola complex in breast reconstruction after nipple-sparing mastectomy: immediate nipple-areola complex reconstruction with banked skin. Plastic Reconstructive Surgery. 2014; 133:73e-74e.

Dent, B. L., et al. Nipple-areolar complex ischemia after nipple-sparing mastectomy with immediate implant-based reconstruction: risk factors and the success of conservative treatment. Aesthetic Surgery Journal. 2014; 34:560-570.

Mori, H., et al. Nipple malposition after nipple-sparing mastectomy and expander-implant reconstruction. Breast cancer. 2016; 23:740-744.

Small, K., et al. Surgical treatment of nipple malposition in nipple sparing mastectomy device-based reconstruction. Plastic Reconstructive Surgery. 2014; 133:57.

Lanier, S. T., et al. The effect of acellular dermal matrix use on complication rates in tissue expander/implant breast reconstruction. Annals of Plastic Surgery. May 2010; 64:674-678.

Ibrahim, A. M, et al. Does acellular dermal matrix really improve aesthetic outcome in tissue expander/implant-based breast reconstruction? Aesthetic Plastic Surgery. 2015; 39:359-368.

Mallon, P., et al. The role of nipple-sparing mastectomy in breast cancer: a comprehensive review of the literature. Plastic Reconstructive Surgery. May 2013; 131(5):969-84.

Lee, K.T., et al. Does the reconstruction method influence development of mastectomy flap complications in nipple-sparing mastectomy? Journal of Plastic Reconstructive & Aesthetic Surgery. 2013, 66(11):1543-50.

Parks, J.W., et al. Human acellular dermis versus no acellular dermis in tissue expansion breast reconstruction. Plastic Reconstructive Surgery. 2012; 130(4)139-46.

McCarthy, C.M., et al. The use of acellular dermal matrices in two-stage expander/implant reconstruction: a multicenter, blinded, randomized controlled trial. Plastic Reconstructive Surgery. Nov. 2012; 130(5 Suppl. 2):57S-66S.

Volden, G. Successful treatment of therapy-resistant atopic dermatitis with clobetasol propionate and a hydrocolloid occlusive dressing. Acta Derm Venereol Suppl. (Stockh). 1992; 176:126-128.

Hochberg, J., et al. A new dressing for skin graft with hydrocolloid and staples. Plastic and Reconstructive Surgery. 1996; 97(5), 1089.

Willems, M. C., et al. Two unusual complications of prone-dependency in severe ARDS. Intensive Care Medicine. 1998; 24(3), 276-277.

* cited by examiner

Table 1  Patient data and statistics.

| Patient | Age | Procedure[b] | Cancer Stage | Ptosis Grade | Breast weight right/left (g) | Intra-Op fill right/left (cc) | Pre-Op nipple right/left (cm) | Pre-Op nipple to IMF right/left (cm) | Time to exchange (weeks) | Nipple position[a] Right/Left | Complication |
|---|---|---|---|---|---|---|---|---|---|---|---|
| Group-1: non-hydrocolloid dressing | | | | | | | | | | | |
| 1 | 54 | Bilateral NSM | IIa | 0 | 245 / 228 | 100 / 100 | 5 / 5 | 5 / 5 | 9 / 9 | -1 / -1 | None |
| 2 | 57 | Bilateral NSM | 0 | 1 | 343 / 465 | 0 / 0 | 9 / 9 | 9 / 9 | 24 / 24 | -1 / -1 | None |
| 3 | 42 | Bilateral NSM | 0 | 1 | 677 / 710 | 0 / 0 | 8 / 8 | 8 / 8 | 22 / 22 | -1 / -1 | Bilateral nipple and mastectomy skin necrosis |
| 4 | 58 | Bilateral NSM | Ia | 1 | 545 / 575 | 200 / 200 | 10 / 10 | 10 / 10 | 18 / 18 | -1 / -1 | Left mastectomy epidermolysis |
| 5 | 43 | Bilateral NSM | 0 | 0 | 200 / 200 | 250 / 250 | 6 / 6 | 6 / 6 | 13 / 13 | -1 / -1 | Bilateral skin necrosis/epidermolysis |
| 6 | 42 | Bilateral NSM | 0 | 2 | 599 / 560 | 0 / 0 | 9 / 9 | 10 / 10 | 26 / 26 | -1 / -1 | Left nipple skin necrosis |
| 7 | 27 | Bilateral NSM | 1a | 2 | 841 / 1064 | 100 / 100 | 8 / 8 | 8 / 8 | 17 / 17 | 0 / -1 | Bilateral nipple epidermolysis and necrosis, Left sided cellulitis |
| 8 | 59 | Bilateral NSM | 0 | 1 | 353 / 329 | 180 / 180 | 6 / 6 | 5 / 5 | 24 / 24 | -1 / -1 | Bilateral nipple and mastectomy skin necrosis |
| 9 | 50 | Bilateral NSM | 0 | 0 | 300 / 283 | 5 / 5 | 6 / 6 | 6 / 6 | 28 / 28 | -1 / -1 | Left nipplel epidermolysis |
| 10 | 66 | Left NSM | Ia | 2 | NA / 350 | NA / 100 | NA / 8 | NA / 8 | 17 / 17 | NA / -1 | None |
| 11 | 54 | Bilateral NSM | 0 | 0 | 150 / 250 | 100 / 100 | 7.5 / 7.5 | 8 / 8 | 17 / 17 | -1 / -1 | Bilateral cellulitis |
| 12 | 37 | Bilateral NSM | Ia | 1 | 490 / 460 | 200 / 200 | 7 / 7 | 6 / 6 | 26 / 26 | -1 / -1 | None |
| 13 | 56 | Left NSM | IIa | - | NA / 420 | NA / 250 | NA / NA | NA / 9 | 22 / 22 | NA / -1 | none |
| 14 | 47 | Bilateral NSM | Ia | 1 | 205 / 222 | 100 / 100 | 5 / 5 | 6 / 6 | 19 / 19 | 0 / 0 | Left nipple skin necrosis |
| 15 | 38 | Bilateral NSM | 0 | 0 | 343 / 323 | 50 / 50 | 6 / 6 | 6 / 6 | 27 / 27 | -1 / -1 | None |
| 16 | 59 | Left NSM | Ia | 1 | NA / 427 | NA / 200 | NA / 11 | NA / 7 | 12 / 12 | NA / 0 | None |
| Average | 51 | | | 0.88 | 419 | 108 | 7.2 | | 20 | 82.8% | 48% |
| Group-2: Hydrocolloid dressing | | | | | | | | | | | |
| 1 | 55 | Bilateral NSM | IIA | 1 | 178 / 200 | 0 / 0 | 5 / 5 | 6 / 6 | 25 / 25 | 0 / 0 | Bilateral nipple epidermolysis |
| 2 | 55 | Bilateral NSM | IA | 1 | 865 / 666 | 0 / 0 | 10 / 10 | 10 / 10 | 19 / 19 | 0 / 0 | None |
| 3 | 39 | Bilateral NSM | 0 | 0 | 470 / 558 | 0 / 0 | 8 / 8 | 8 / 8 | 17 / 17 | 0 / 0 | None |
| 4 | 64 | Bilateral NSM | IIa | 1 | 210 / 180 | 0 / 0 | 5 / 5 | 5 / 5 | 12 / 12 | 0 / -1 | None |
| 5 | 36 | Bilateral NSM | Ia | 2 | 331 / 273 | 150 / 150 | 8 / 8 | 8 / 8 | 16 / 16 | 0 / 0 | None |
| 6 | 58 | Bilateral NSM | 0 | 1 | 395 / 300 | 0 / 0 | 6 / 6 | 6 / 6 | 22 / 22 | 0 / 0 | None |
| 7 | 70 | Bilateral NSM | 0 | 2 | 825 / 450 | 0 / 0 | 11 / 11 | 8 / 8 | 18 / 18 | 0 / 0 | Bilateral nipple and mastectomy skin Necrosis |
| Average | 54 | | | 1.1 | 422 | 21 | 7.4 | | 19 | 7.1% | 29% |
| P-Value | 0.37 | | | 0.41 | 0.97 | 0.0016 | 0.72 | | 0.54 | 3x10-6 | 0.33 |

[a] Nipple position- 0 = nipple at point of maximal projection on lateral view, -1 = nipple lower then point of maximal projection o lateral view.
[b] Nipple sparing mastectomy (NSM).

FIG. 2

HYDROCOLLOID DRESSING FOR PRECISE NIPPLE POSITIONING AFTER NIPPLE- OR SKIN-SPARING MASTECTOMY

CROSS-REFERENCE TO RELATED APPLICATIONS

This nonprovisional application claims priority to U.S. Provisional Patent Application No. 62/214,344, entitled "Hydrocolloid Dressing for Precise Nipple Positioning Post-Nipple Saving Mastectomy", filed Sep. 4, 2015 by the same inventors, the entirety of which is incorporated herein by reference.

BACKGROUND OF THE INVENTION

1. Field of the Invention

This invention relates, generally, to nipple-sparing mastectomies (NSM) and skin-sparing mastectomies (SSM). More specifically, it relates to correcting nipple position and eliminating necrotic complications following NSM and SSM.

2. Brief Description of the Prior Art

NSM is a recently developed but widely utilized technique that can produce aesthetically pleasing reconstruction results after mastectomy. Different methods of reconstruction include immediate reconstruction with implants, reconstruction using autologous tissues, and reconstruction using tissue expanders with delayed exchange for implants. An example of such a method with NSM is the tissue expander reconstruction method (Mallon P, et al. The role of nipple-sparing mastectomy in breast cancer: a comprehensive review of the literature. Plast Reconstr Surg 2013, 131(5): 969e84). Its benefits include a more natural appearing result and improved patient satisfaction. Key components of this technique are maintenance of nipple-areolar complex (NAC) and mastectomy skin flap viability, as well as proper nipple position and symmetry (Lee K T, et al. Does the reconstruction method influence development of mastectomy flap complications in nipple-sparing mastectomy? J Plast Reconstr Aesthet Surg 2013, 66(11):1543-50). Nipple position and healthy mastectomy flaps with good vascularity are important determinants of a successful aesthetic final result and patient satisfaction.

Nipple malposition is a common complication of NSM. A recent study (Mori H, Uemura N, Okazaki M, et al. Nipple malposition after nipple-sparing mastectomy and expander-implant reconstruction. Breast Cancer 2015) correlated the NAC malposition to breast ptosis index. In their study, ptotic breasts and NAC malposition were so common that the surgeon is expected to perform ancillary procedures to reposition the nipple in every case (Mori H, Uemura N, Okazaki M, et al. Nipple malposition after nipple-sparing mastectomy and expander-implant reconstruction. Breast Cancer 2015). Another study that looks at nipple malposition after NSM found that 13% had nipple malpositioning and significantly correlated them with factors including larger pre-operative sternal notch to nipple distance, and post-operative NAC ischemia (Kelly K, Small K, Swistel A, et al. Abstract 47: surgical treatment of nipple malposition in nipple sparing mastectomy device-based reconstruction. Plast Reconstr Surg 2014; 133:57).

NSM with infra-mammary fold incisions can provide excellent cosmesis. The main complication is related to decreased mastectomy flap circulation, leading to partial or total nipple or skin necrosis. NAC necrosis can cause lack of projection, hypopigmentation, scarring and distortion (Park S W, Lee T J, Kim E K, et al. Managing necrosis of the nipple-areola complex in breast reconstruction after nipple-sparing mastectomy: immediate nipple-areola complex reconstruction with banked skin. Plast Reconstr Surg 2014; 133:73e-74e). Single stage reconstruction would likely cause too much tension on mastectomy flaps and could potentially lead to this irreversible problem. As outlined in other studies, cutaneous blood flow increases whenever there's less expansion. This principle could conceivably apply to tissue expanders with high initial fill (Dent B L, Small K, Swistel A, et al. Nipple-areolar complex ischemia after nipple-sparing mastectomy with immediate implant-based reconstruction: risk factors and the success of conservative treatment. Aesthet Surg J 2014; 34:560-570).

Acellular dermal matrix (ADM) is commonly used to augment reconstructions in an effort to maximize proper skin envelope fill, draping, and nipple position (Mallon P, et al. The role of nipple-sparing mastectomy in breast cancer: a comprehensive review of the literature. Plast Reconstr Surg 2013, 131(5):969-84; Parks J W, et al. Human acellular dermis versus no acellular dermis in tissue expansion breast reconstruction. Plast Reconstr Surg 2012, 130(4):739-46; Salzberg C A, Focus on technique: one-stage implant-based breast reconstruction. Plast Reconstr Surg 2012, 130(5 Suppl. 2):95S-103S; McCarthy C M, et al. The use of acellular dermal matrices in two-stage expander/implant reconstruction: a multicenter, blinded, randomized controlled trial. Plast Reconstr Surg 2012, 130(5 Suppl. 2):57S-66S). ADM allows higher initial tissue expander fill volumes, though can also lead to increased risks of complications, explantations, and infections (Lanier S T, Wang E D, Chen J J, et al. The effect of acellular dermal matrix use on complication rates in tissue expander/implant breast reconstruction. Ann Plast Surg 2010; 64:674-678). Their aesthetic advantages of lower pole expansion, definition of IMF, and better cosmetic outcome justify its cost, though its potential complications are still a topic of discussion (Ibrahim A M, Koolen P G, Ganor O, et al. Does acellular dermal matrix really improve aesthetic outcome in tissue expander/implant-based breast reconstruction? Aesthetic Plast Surg 2015; 39:359-368).

Lack of attention to certain details in ADM can lead to difficult-to-correct nipple asymmetries, which compromise the overall result (Salzberg C A, Focus on technique: one-stage implant-based breast reconstruction. Plast Reconstr Surg 2012, 130(5 Suppl. 2):95S-103S). Further, NAC necrosis is reported as 2.5-60% in different series of NSM. The predictive factors associated with NAC necrosis that is resistant to conservative treatment include ADM and single stage breast reconstruction (Dent B L, Small K, Swistel A, et al. Nipple-areolar complex ischemia after nipple-sparing mastectomy with immediate implant-based reconstruction: risk factors and the success of conservative treatment. Aesthet Surg J 2014; 34:560-570). NAC necrosis can cause irreversible scarring and poor reconstructive outcomes after NSM. Close collaboration with the breast surgeon is essential with NSM. Despite this, the mastectomy skin flaps are often very thin depending on patient, tumor and breast surgeon preference. Oftentimes, there are thin areas within mastectomy flaps that are otherwise seemingly viable.

Significant intraoperative fill is also required to facilitate the hand-in-glove fit needed in ADM use to minimize complications (Salzberg C A, Focus on technique: one-stage implant-based breast reconstruction. Plast Reconstr Surg 2012, 130(5 Suppl. 2):95S-103S; McCarthy C M, et al. The use of acellular dermal matrices in two-stage expander/implant reconstruction: a multicenter, blinded, randomized controlled trial. Plast Reconstr Surg 2012, 130(5 Suppl. 2):57S-66S). However, the goal of maximizing fill runs in direct opposition to maximizing tissue viability due to increased tension in the setting of compromised perfusion (Parks J W, et al. Human acellular dermis versus no acellular dermis in tissue expansion breast reconstruction. Plast Reconstr Surg 2012, 130(4):739-46; Salzberg C A., Focus on technique: one-stage implant-based breast reconstruction. Plast Reconstr Surg 2012, 130(5 Suppl. 2):95S-103S).

That being said, the use of high intraoperative fill volumes is the leading method in NSM reconstruction to improve precision of nipple placement. High fill volume produces a more natural breast mound appearance post-operatively. However, as noted, higher fill rates also carry much greater risks of complication, such as nipple or skin necrosis, epidermolysis, and flap failure due to increased tissue stress. ADM may be used in cases of high intraoperative fill to help improve nipple positioning, but this routine is also associated with high complication rates. Even minor necrotic events can be traumatic to the patient and costly to repair.

The safer option to reduce necrotic complications due to tissue stress would be to minimize intra-operative fill during the initial mastectomy. This would enhance tissue circulation, protect the viability of the tissue, and eliminate the need for ADM. However, low intraoperative fill rates can often lead to redundant skin and poor skin envelope draping, which can scar poorly and cause displacement of the nipple, specifically nipple placement being lower than desired.

Accordingly, what is needed is an apparatus and method for resolving incorrect nipple position and necrotic complications following NSM or SSM. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for improved nipple positioning post-NSM/SSM is now met by a new, useful, and nonobvious invention.

In an embodiment, the current invention is a method of elevating and positioning a nipple/nipple-areolar complex of a patient after a NSM or a SSM. A hydrocolloid dressing is provided for positioning over a breast of the patient (the breast having undergone the NSM or SSM). The dressing has a main body and a strap extension. An aperture is created in the main body of the dressing, where the aperture corresponds to a desired post-NSM/SSM nipple position on the patient's breast. The dressing is secured over the patient's breast, specifically with the dressing's main body disposed over the breast mound, the strap extension extending toward or over the patient's shoulder, and the patient's nipple disposed within the dressing's aperture. It should be noted that the NSM/SSM incision site typically remains uncovered by the dressing.

After being secured, the dressing is fully extended or otherwise has no creases in it. With the dressing in place, the afflicted breast skin and tissue can heal within a wound healing environment between the breast and dressing, thus also permitting the patient's nipple to be positioned in the desired position. The patient's nipple can then be evaluated to determine whether the desired position has been reached. The foregoing methodology can be done without use of any acellular dermal matrix or intraoperative fill after the NSM/SSM.

If there are changes in skin folds or nipple positioning, the breast skin can be manipulated superiorly and draped toward the patient's shoulder. In a further embodiment, if the nipple does not result in the desired position, the dressing can be removed from the patient and replaced with an inverted-Y or -V hydrocolloid dressing. This subsequent dressing has a shoulder component and two (2) branched extensions extending inferiorly from the shoulder component. The dressing would be secured to the patient's breast with one branched extension on one side of the nipple and the other branched extension on the opposite side of the nipple, and the shoulder component is disposed on the patient's shoulder. With this dressing in place, the breast skin and tissue can heal to position the patient's nipple in the desired position.

In certain embodiments, situations arise where a bilateral NSM/SSM was performed on the patient. In this case, similar hydrocolloid dressings (both types described) can be used and applied in a similar manner to the methodology described previously. The hydrocolloid dressings for both breasts should be mirror images of each other. This would allow the skin and tissue in both afflicted breasts to heal in similar manners, thus providing breasts that are symmetrical to each other and are aesthetically pleasing.

One manner of securing the dressing over the patient's breast is by adhering an inferior edge of the dressing and continuing to adhere the dressing to the breast in a superior direction until the strap extension and/or shoulder component is adhered to the patient's shoulder. Now referring to positioning the patient's nipple within the dressing's aperture, this step can be performed by pulling and draping redundant mastectomy skin with the nipple superiorly toward the patient's shoulder until the nipple is disposed within the aperture.

In a separate embodiment, the current invention is a method of elevating and positioning a nipple of a patient after a bilateral NSM/SSM without use of acellular dermal matrix or intraoperative fill after said nipple-sparing mastectomy. The method can include any one or more, or even all, of the foregoing characteristics and features described. In certain embodiments, the inventive method can include performance of the NSM/SSM itself.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 2 is a table of patient data and statistics for a study described herein.

DETAILED DESCRIPTION OF THE PREFERRED EMBODIMENT

Figure 1A:
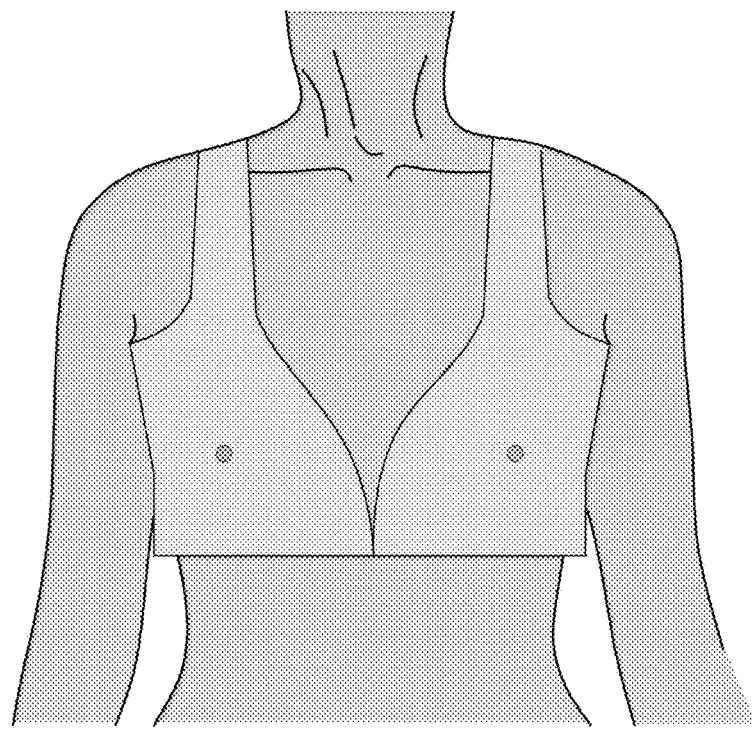
FIG. 1A depicts a hydrocolloid bra design, according to an embodiment of the current invention.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

Complete tissue preservation is of paramount importance in NSM where skin and nipple necrosis can compromise the ability to obtain an aesthetic result. Forgoing the use of ADM and large intraoperative fills and relying instead on minimal intraoperative fill and total sub-muscular expander placement places the least amount of stress on NSM tissue but can result in a significant amount of nipple malposition that can be challenging to correct. However, when combined with a hydrocolloid dressing, which provides an adherent non-compressive dressing, precise skin draping, and proper nipple placement, according to the current invention, these challenges can be overcome and tissue perfusion maximized.

In an embodiment, the current invention is a hydrocolloid dressing and associated methodology that results in both mastectomy skin tissue health and aesthetic success with optimal nipple positioning. With the hydrocolloid dressing, several unexpected benefits were achieved. For example, the NAC was stabilized in the desired high position, ptosis was reduced, and with no intra-operative fill, complications were decreased. Further, by eliminating the need for ADM and intra-operative fill, the technique using the hydrocolloid dressing decreased the rate of complications.

Use of total sub-muscular coverage instead of ADM not only eliminated ADM-related complications but also decreased operative time and cost—all increasingly important concerns in today's health care system. Alternative conventional methodologies include suturing the nipple to the underlying muscle, which does not address skin excess, and post-operative bra/wraps, which place undue pressure on the flaps. Despite the excellent results reported with ADM reconstruction, a significant number of patients would routinely present with compromised mastectomy flaps that will need to be managed conservatively. As noted by Salzberg et al., management of questionable skin viability intra-operatively should push the surgeon toward sub-muscular placement with little to no intraoperative fill (Salzberg C A., Focus on technique: one-stage implant-based breast reconstruction. Plast Reconstr Surg 2012, 130(5 Suppl. 2):95S-103S).

In an embodiment, the current invention is an apparatus and method/technique that uses a hydrocolloid bra (i.e., support, dressing) that results in both improved circulation and aesthetic success with optimal nipple positioning. By applying and adhering the hydrocolloid dressing to the mastectomy flaps, where the hydrocolloid dressing has specific patterns, stability of the nipple-areolar complex (NAC) in the desired higher position can be achieved. Having proper positioning of the NAC would eliminate the need for ADM and intra-operative fill, and as a result decrease the stress on the mastectomy flaps and decrease ptosis. Using the hydrocolloid dressing, the skin remained well-perfused and protected after NSM, despite not using ADM or initial fill volume to hold the nipple in a high position during healing. These results were highly unexpected, as will become clearer as this specification continues.

Figure 1B:
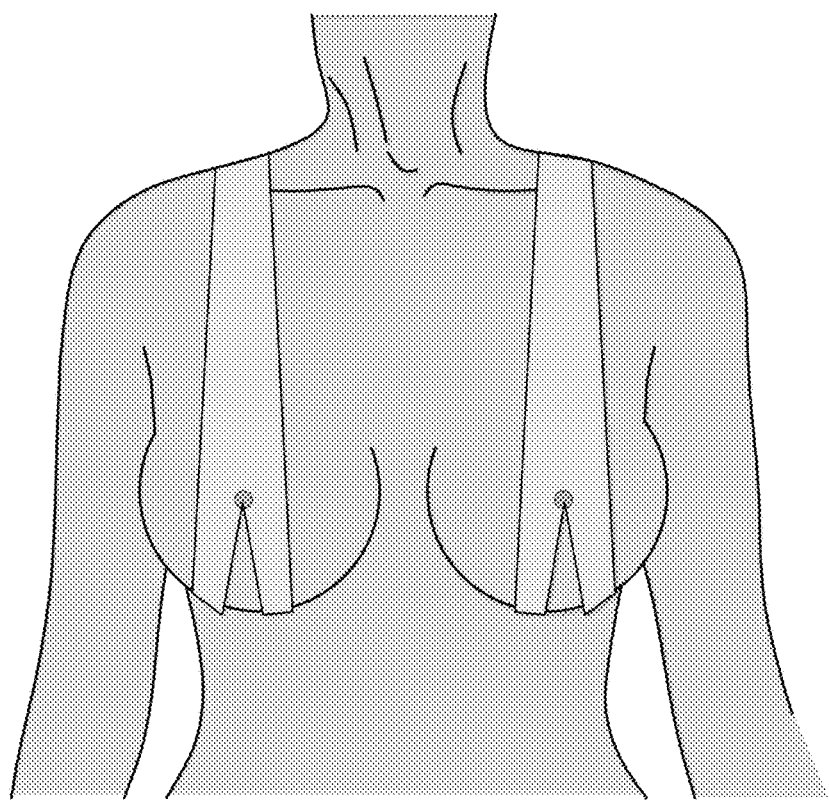
FIG. 1B depicts an alternative inverted-Y hydrocolloid bra design, according to an embodiment of the current invention.
Figure 1C:
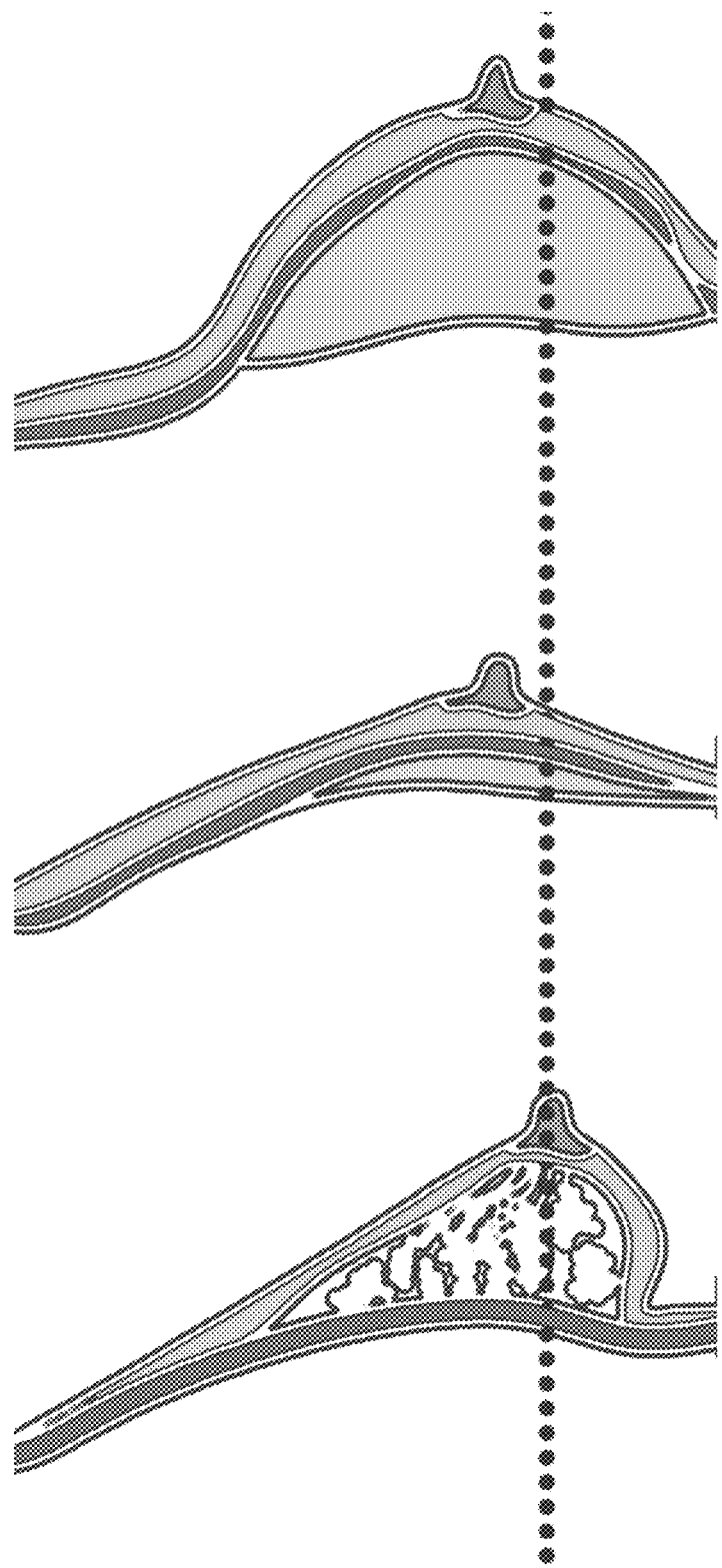
FIG. 1C depicts improvement of ptosis by elevating the NAC.

In operation, the hydrocolloid dressing (exemplary designs can be seen in FIGS. 1A-1B) is placed over the breast after surgery, and remains in place for a suitable amount of time, for example at least approximately two weeks. After about one month, the tissue expansion phase begins and expanders are filled weekly, as is known in the art. The hydrocolloid dressing can be applied on either side or both sides of the nipple during expansion phase to precisely control nipple position. Elevation of the NAC improves ptosis (see FIG. 1C where ptosis can be seen in the leftmost image and elimination of ptosis can be seen in the rightmost image with NAC elevated).

In the studies described in this specification, treatment with a hydrocolloid dressing according to certain embodiments of the current invention, as opposed to conventional methods, reduced the odds of incorrect nipple positioning significantly, specifically by about 97%. Because the current methodology eliminates the need for intraoperative fill and ADM, the hydrocolloid dressing and associated methodology also reduced the odds of necrotic complications significantly, specifically by about 70%. This extremely high level of success of correct nipple positioning without intraoperative fill or ADM was not expected, based on the conventional art, which has made it well-known that intraoperative fill and/or ADM is needed for optimal nipple placement post-NSM/SSM. The hydrocolloid dressing applied after NSM with no ADM and no intraoperative fill is an efficient and extremely effective method/technique to achieve precise nipple placement, while also protecting the viability of the overlying tissue.

As can be seen herein, the current invention is described and illustrated in use after a NSM procedure. However, it can be understood that the hydrocolloid dressing can also be used after a SSM procedure as well, in a substantially similar manner as used after a NSM procedure. Thus, it is contemplated herein that the instant specification enables use of the current hydrocolloid dressing after a SSM by virtue of enabling its use after a NSM.

Study 1

A novel use of hydrocolloid dressing (e.g., manufactured by CONVATEC DUODERM) is presented herein as a method to accurately drape mastectomy skin and position the NAC after NSM without the use of ADM or intraoperative fill.

Patient data was collected retrospectively from a prospectively-maintained IRB-approved breast reconstruction database. Included were consecutive patients undergoing NSM with total sub-muscular tissue expander placement without ADM. All patients were from a single reconstructive surgeon's practice at a teaching institution.

Patients were split into two (2) groups. Group 1 represented the control group and included consecutive patients that did not receive the post-operative hydrocolloid dressing. Group 2 represented the variable group and included consecutive patients treated with the hydrocolloid dressing. Descriptive data was collected and is listed in FIG. 2. Nipple position was assessed on anterior-posterior (AP) and lateral photographs taken immediately prior to implant exchange. Nipple position was graded as 0 if it was located on the most projected point of the breast mound, and −1 if lower on the breast mound.

Figure 3:
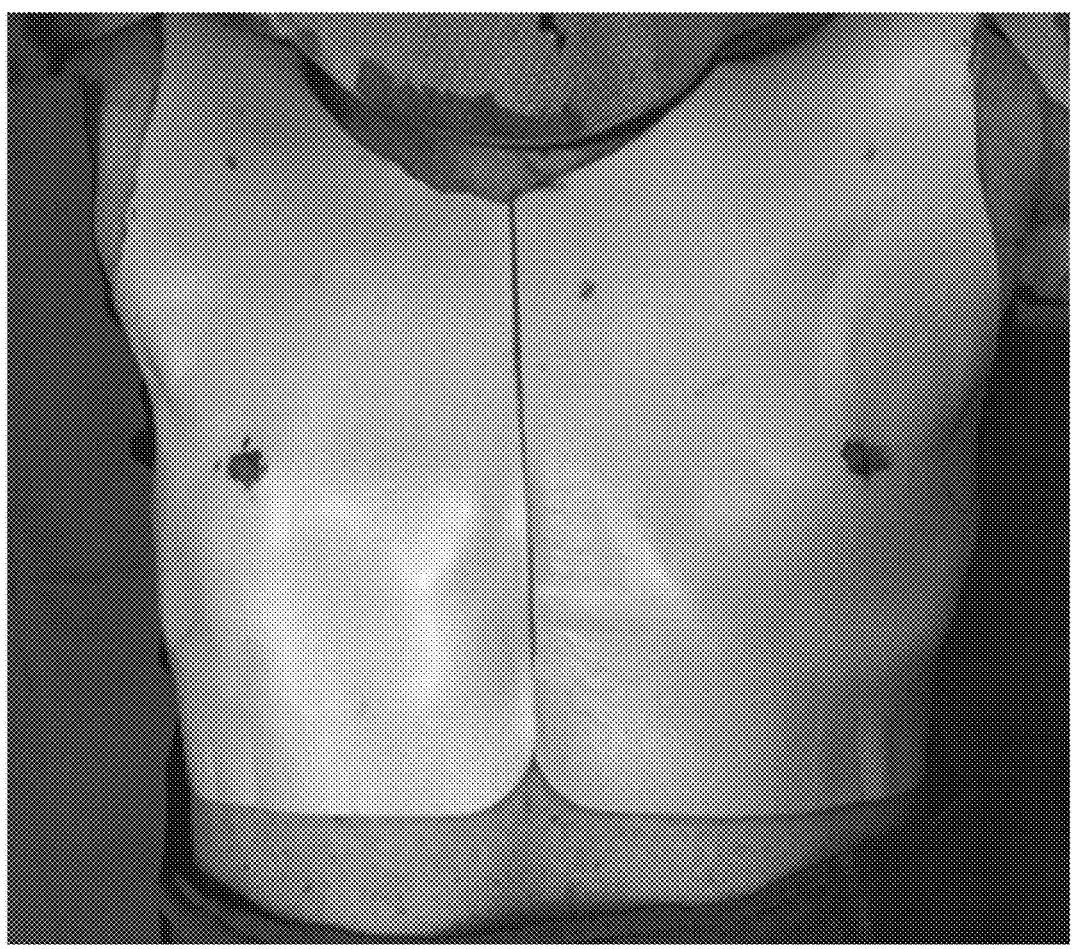
FIG. 3 is an image with a hydrocolloid bra/dressing in place, according to an embodiment of the current invention.

Group 2 patients had the hydrocolloid dressing fashioned for each breast to cover the entire mastectomy flap up to the shoulders. A small window over the nipple was cut to ensure accurate placement, as seen in FIG. 3. Redundant mastectomy skin with the NAC was draped superiorly towards the shoulder with accurate location of NAC over the center of the tissue expander. The dressing remained in place for approximately one week. Descriptive statistics were performed on both study groups. A p-value of <0.05 was considered statistically significant.

Twenty-nine (29) breasts on sixteen (16) patients met criteria for Group 1, while fourteen (14) breasts on seven (7) patients met criteria for Group 2 (see FIG. 1). There were no significant differences between groups in regard to age (p=0.37), ptosis (p=0.41), breast weight (p=0.97), and nipple-to-IMF (inframammary fold) distance (p=0.72). A significant difference was noted for intraoperative fill volume (p=0.0016). For Group 1, intraoperative fills were employed at the surgeon's discretion to assist in filling the skin envelope, while only the first patient in Group 2 (patient #5) received an intraoperative fill during the transition to use of the hydrocolloid dressing. Length of time to exchange tissue expander for permanent implant was not found to be significantly shorter for Group 1 (p=0.54). Regarding nipple position, 82.8% of patients in Group 1 (no hydrocolloid dressing) were found to have inferiorly-displaced nipples, and only 7.1% of patients in Group 2 (draped hydrocolloid dressing) were found to have inferiorly-displaced nipples (p=$3\times10^{-6}$). Complications observed included epidermolysis, cellulitis, and skin/nipple necrosis and were found to be lower in Group 2. Specifically, about 48% of patients in Group 1 were observed to have complications, and only about 29% of patients in Group 2 were observed to have complications. Though a lower incidence of complications were observed in Group 2, the reduction was not found to be statistically significant (p=0.33). No total nipple losses were reported.

Use of this technique using the hydrocolloid dressing resulted in significant improvement of nipple position compared to standard techniques (p=$3\times10^{-6}$) and was applicable to patients with grade 0-2 ptosis and breast weight of 178-865 g. Accordingly, the technique according to the current invention using the hydrocolloid dressing without ADM provides several benefits that resolve many of the issues experienced by the conventional art.

Study 2

Subjects/Patients

After IRB approval, thirty-five (35) consecutive patients with a total of 63 breasts undergoing NSM with subsequent tissue expander reconstructions were performed and evaluated after IRB approval. All surgeries were performed at Moffitt Cancer Center (Tampa, Fla.) by the same plastic surgeon but different surgical oncologists. Patients were evaluated in two groups based on whether they had received no intraoperative fill with post-operative hydrocolloid dressing (test group) or some levels of intraoperative fill without hydrocolloid dressing (control group). Patients with ADMs were excluded.

Age, ptosis grade, pre-operative nipple to IMF (R/L), tumor characteristics (size), mastectomy specimen weight (R/L) in grams, time from mastectomy to first fill, time from mastectomy to final fill, final fill volume (R/L), NAC and skin necrosis, and other complications were recorded. Post-operative photographs for NAC positioning were assessed using a scoring system for optimum nipple positioning. Nipple position correctness was determined by assessment of post-operative photographs using a scoring system. For the "correct" status to be applied, the nipple should be at the most projected point of the breast mound, based on a side view. This status would not be applied if the nipple was positioned at a lower point. Measurements of pre-operative nipple to infra-mammary fold and ptosis grade were also recorded. Complications were defined as NAC necrosis or epidermolysis, or any other problem resulting from the procedure that required return to the operating room within one (1) month of mastectomy. Patient information was de-identified and quantified prior to data analysis. The two groups were then compared to assess the benefits of using the hydrocolloid dressing according to certain embodiments of the current invention.

Application of Hydrocolloid Dressing and Post-Op Care

The current study was performed as a retrospective cohort study to evaluate the success of the technique using a hydrocolloid bra/dressing for better nipple position and reduced complications in patients who underwent NSM with tissue expander reconstruction.

The following is a non-limiting example of the specific steps to be taken during NSM and when applying the hydrocolloid dressing after NSM.

The NSM is completed using the infra-mammary incisions. A sub-pectoral pocket is created. Tissue expanders are placed in the sub-muscular pocket without using ADM. Once tissue expanders are fully covered with muscle, a drain is placed, skin edges are freshened, and mastectomy skin viability is checked. No intra-operative fill is done. The incisions are closed in two layers.

Due to the absence of intra-operative fill, the skin is not inappropriately stretched and can heal under minimal stress. During this time, breast skin may appear redundant.

Figure 4A:
FIG. 4A depicts a hydrocolloid bra designed for a patient, according to an embodiment of the current invention. A cut of the current hydrocolloid bra is prepared in a shape capable of covering the breast like a bra top, while leaving the incision site uncovered and allowing the nipple to protrude.
Figure 4B:
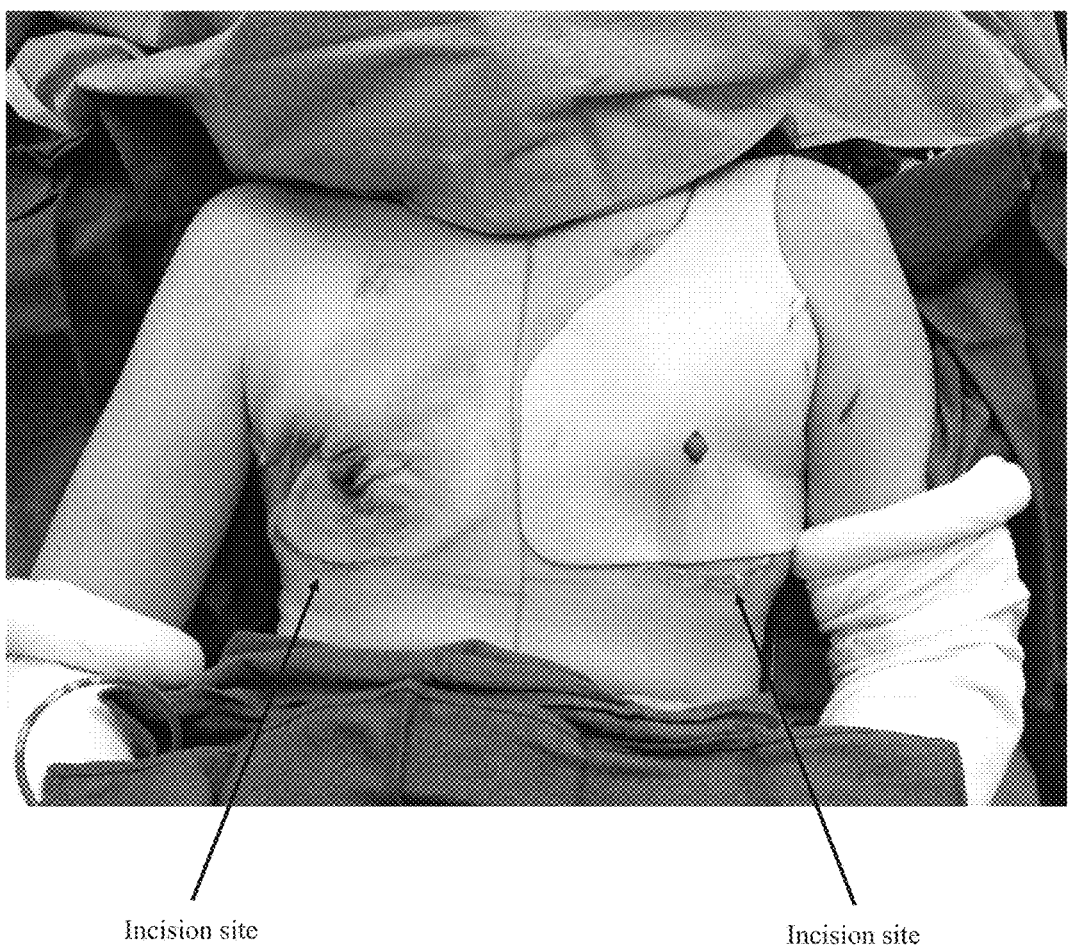
FIG. 4B is a post-operative photograph of a patient after bilateral NSM. The stress on the mastectomy skin should be noted. The hydrocolloid bra of FIG. 4A is applied to one breast.
Figure 4C:
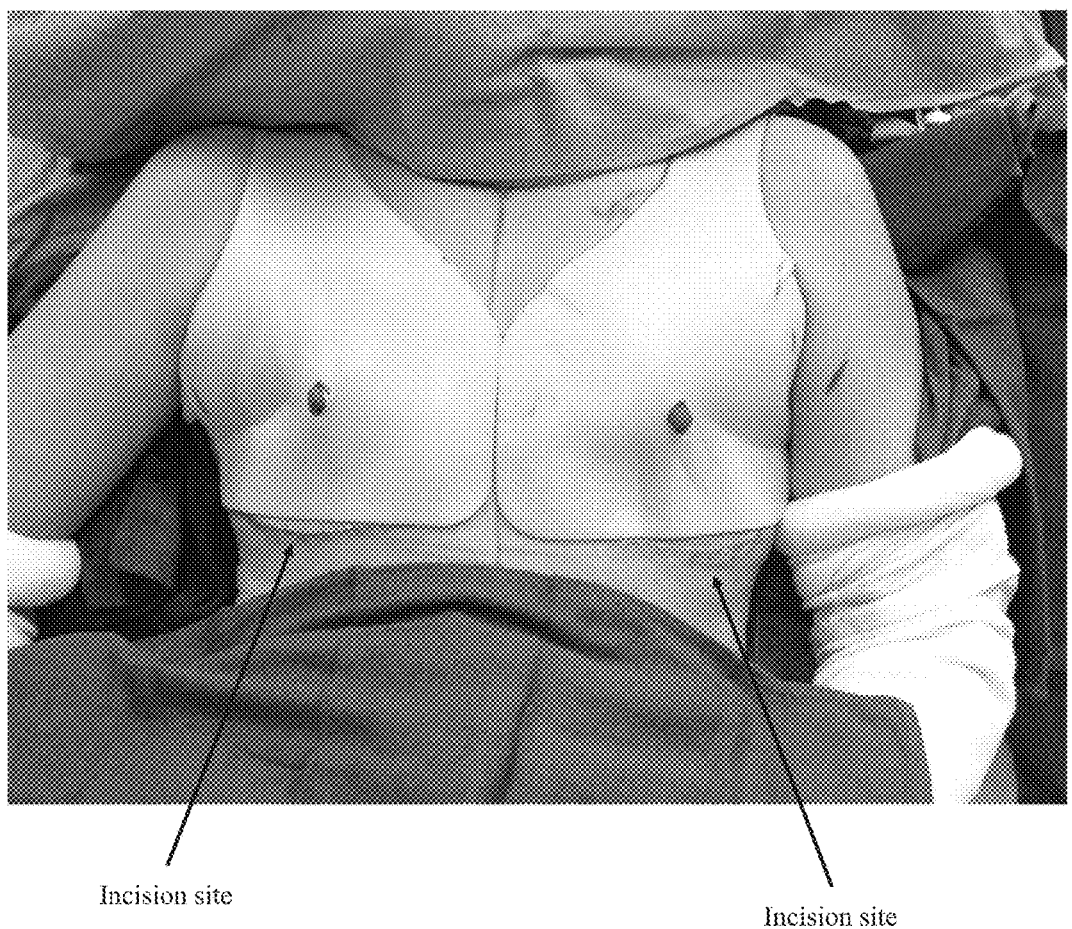
FIG. 4C depicts bilateral placement of the hydrocolloid bra of FIG. 4A. Once the bra is completed, the rear adhesive cover is removed and the hydrocolloid bra is applied to the breast. Adhesion starts from bottom and continues upward toward the top, taking care to not leave any creases in the dressing on the skin. The holes that are cut correspond to each nipple and are placed accordingly. Once the main base of the design is applied, the strap extensions are placed over shoulders, similar to bra straps.

The patient is placed in about an 80° sitting position on the operating table. A hydrocolloid sheet is designed to identify the new higher location of the NAC (see FIG. 4A). The hydrocolloid dressing is prepared in a shape capable of covering the breast similar to a bra top, while leaving the incision site uncovered, as in FIGS. 4B-4C. If bilateral, the design of the hydrocolloid dressing should be patterned symmetrically (see FIG. 4C). Additionally, small apertures are cut out at the new/desired location of the nipple.

When the final design of the hydrocolloid dressing is completed, the adhesive backing is removed, and the hydrocolloid dressing is applied to the breast with adhesive side on the breast skin. Application of the flexible dressing is adhered to the breast from an inferior edge, continuing upward along the breast toward the superior edge of the dressing. There should be no creases in the dressing when adhered to the breast. In other words, the dressing should be fully extended upon application.

Careful attention should be given to placement of the patient's nipple in the nipple aperture of each hydrocolloid dressing. Once the main base of the dressing is applied, the strap extensions are followed over the shoulders, similar to bra straps. This superior vector traction holds the NAC in a high position during healing and ensures that it will remain at the point of maximal projection as the tissue expands and as it fully heals. A second hydrocolloid dressing is positioned on the opposite breast in a substantially similar manner if a bilateral NSM was performed. The two hydrocolloid dressings should mirror each other across the patient's chest. With the hydrocolloid dressing(s) covering the entire mastectomy skin, there should be no creases, each NAC should be aligned appropriately, and each infra-mammary fold incision should be left uncovered.

This design of the hydrocolloid dressing and associated methodology allows direct visual assessment of the NAC and allows alignment to be parallel and in a desired location in bilateral NSM. It also creates a wound healing environment for the thin mastectomy flaps to heal. Incision, nipple viability, and fluid collections are easily checked with the dressing in place during the post-operative hospital stay.

Patients can be discharged from the hospital with the hydrocolloid dressing in place. This post-operative dressing can stay in place for about one (1) week, and then it can be changed by the physician to a new hydrocolloid dressing. The new dressing can then be left in place for approximately another week. Patients can be informed not to get the dressing wet. Following this two-week period, the dressing is removed. By this time, the mastectomy flaps should have adhered to the underlying muscle in a desired position with NAC properly aligned.

Figure 5A:
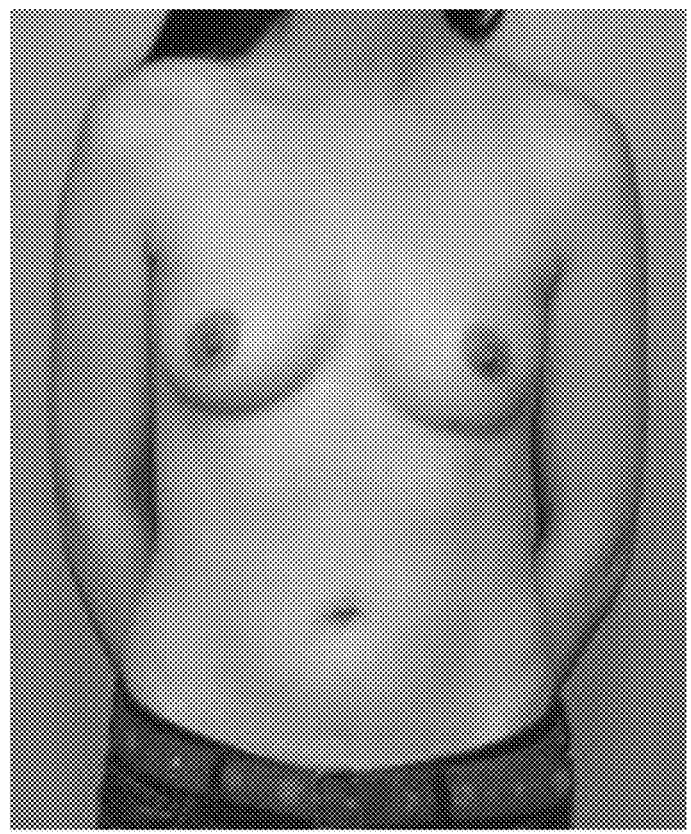
FIG. 5A is a pre-operative photograph of a patient before bilateral NSM.
Figure 5B:
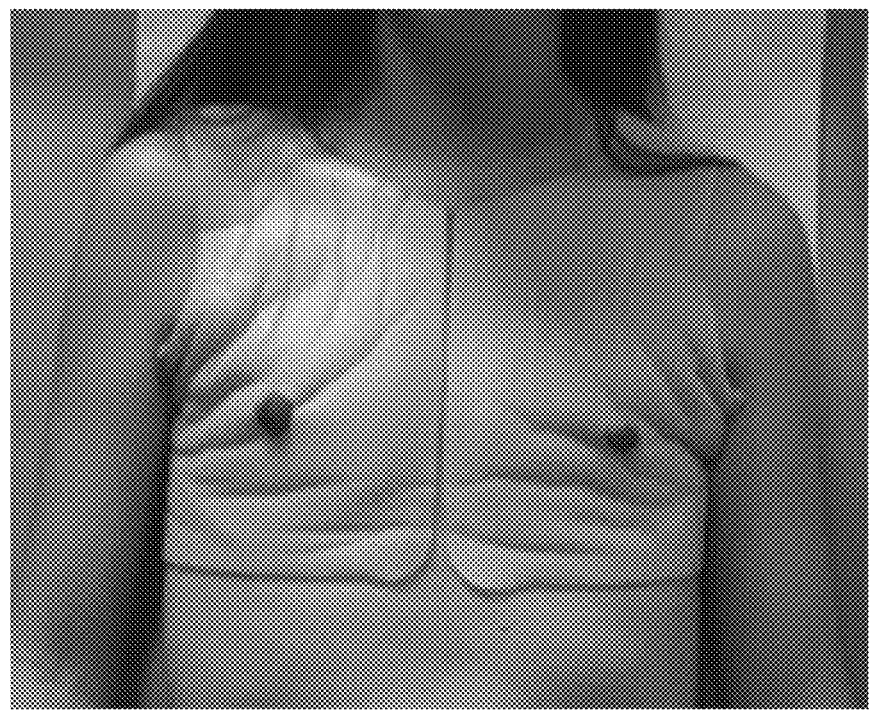
FIG. 5B depicts a hydrocolloid bra positioned immediately after bilateral NSM and total sub-muscular placement of expanders without use of ADM after NSM.
Figure 5C:
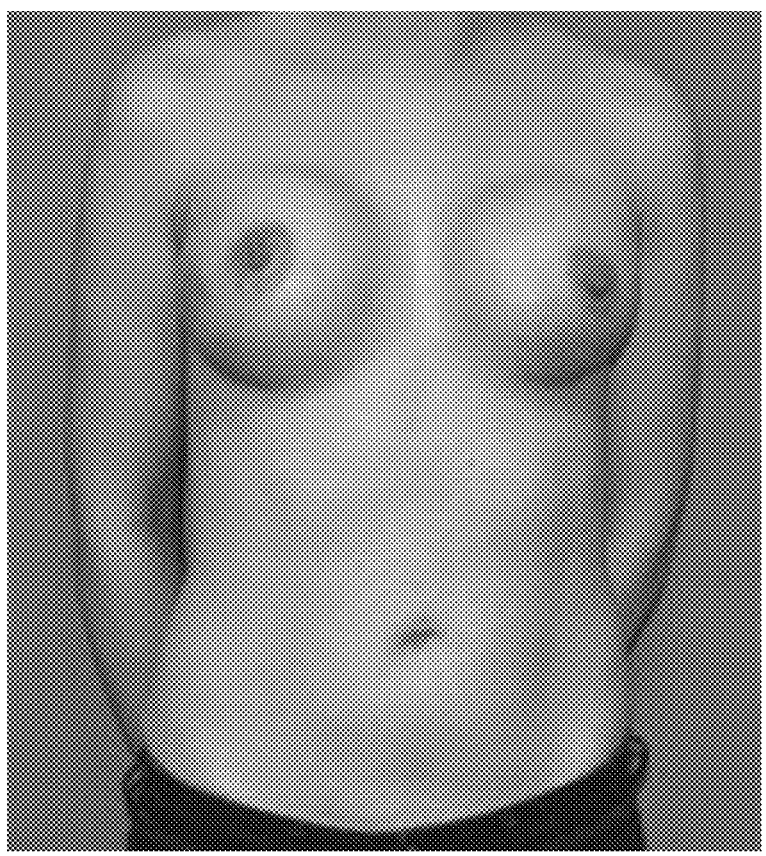
FIG. 5C depicts the breasts with total sub-muscular expanders fully expanded without use of ADM after NSM.
Figure 5D:
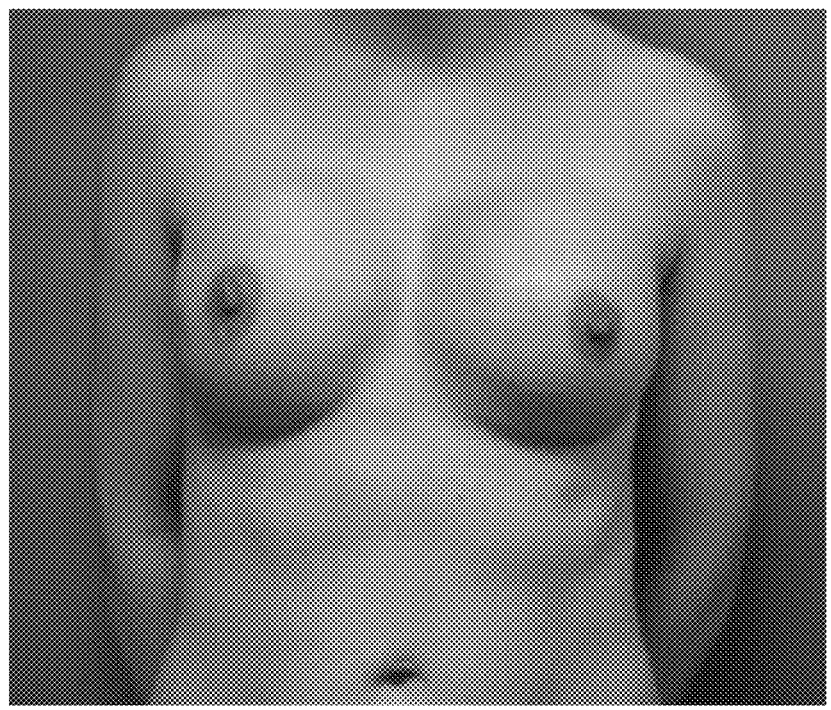
FIG. 5D depicts the breasts with tissue expanders replaced by permanent implants, completed without need for other revisional surgeries.
Figure 6A:
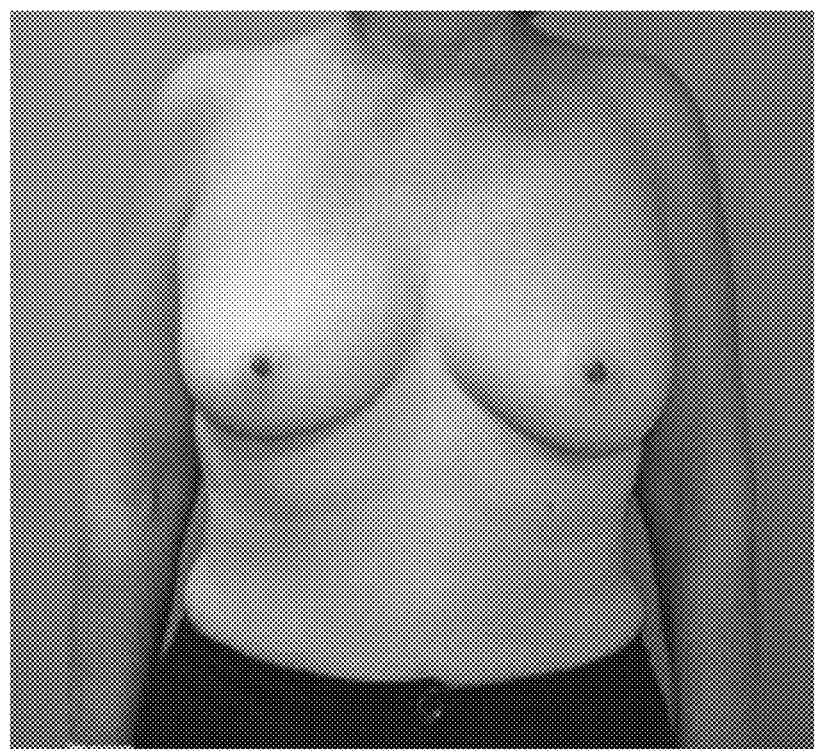
FIG. 6A is a pre-operative photograph of a patient before bilateral NSM.
Figure 6B:
FIG. 6B depicts a hydrocolloid bra positioned immediately after bilateral NSM and total sub-muscular placement of expanders without use of ADM after NSM.
Figure 6C:
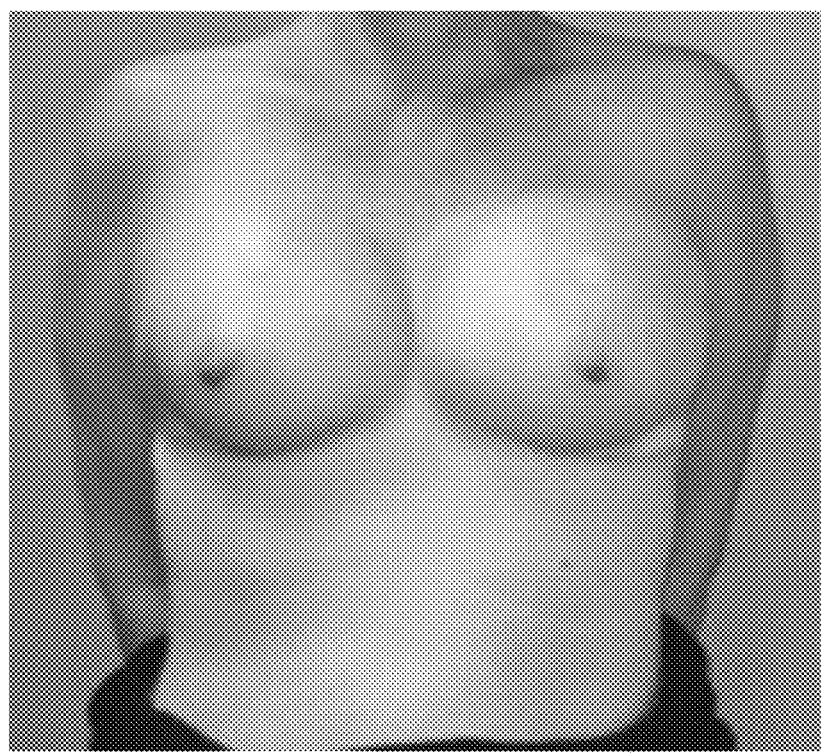
FIG. 6C depicts the breasts with total sub-muscular expanders fully expanded without use of ADM after NSM.
Figure 6D:
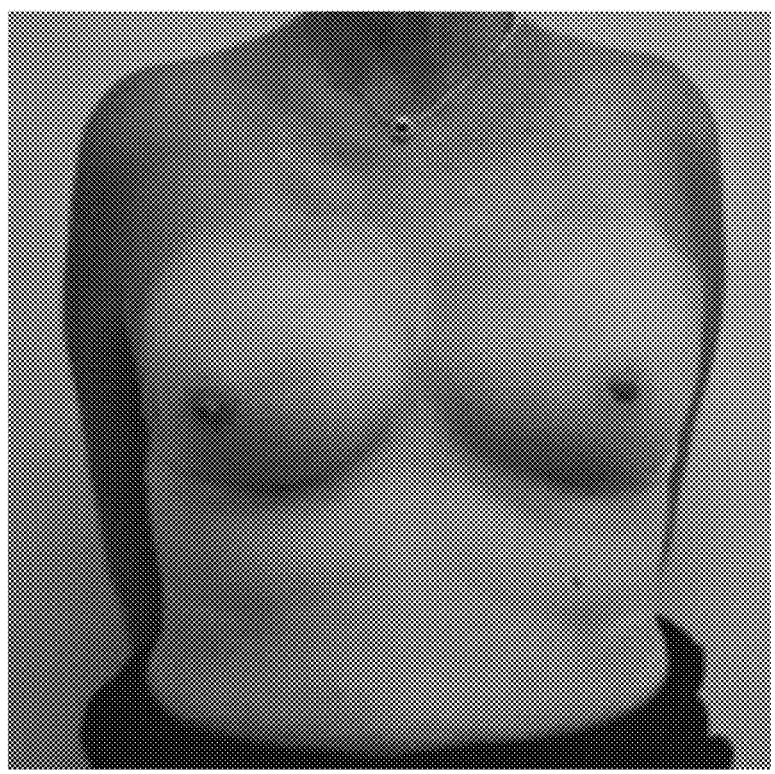
FIG. 6D depicts the breasts with tissue expanders replaced by permanent implants, completed without need for other revisional surgeries.
Figure 7A:
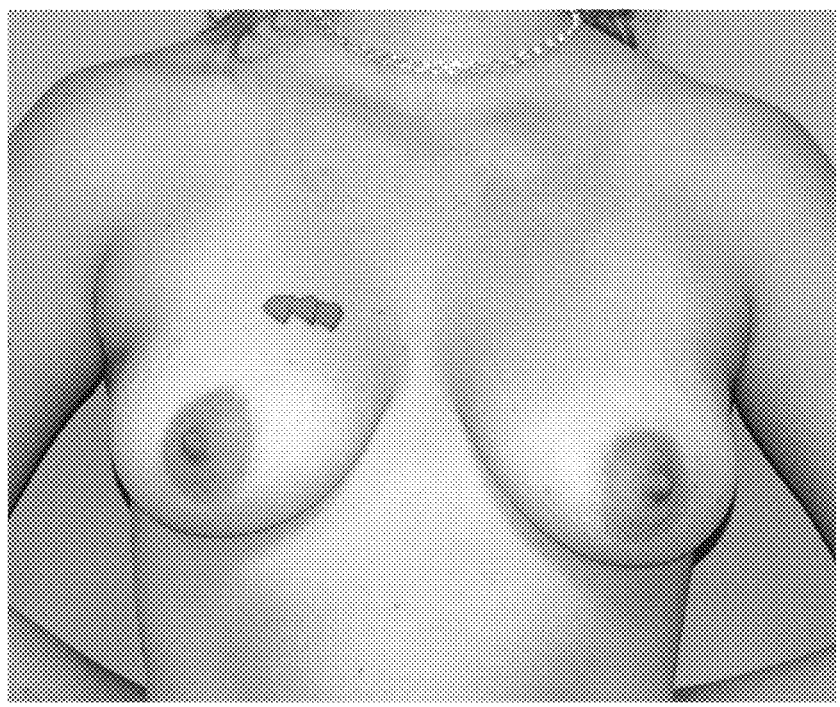
FIG. 7A is a pre-operative photograph of a patient before bilateral NSM.
Figure 7B:
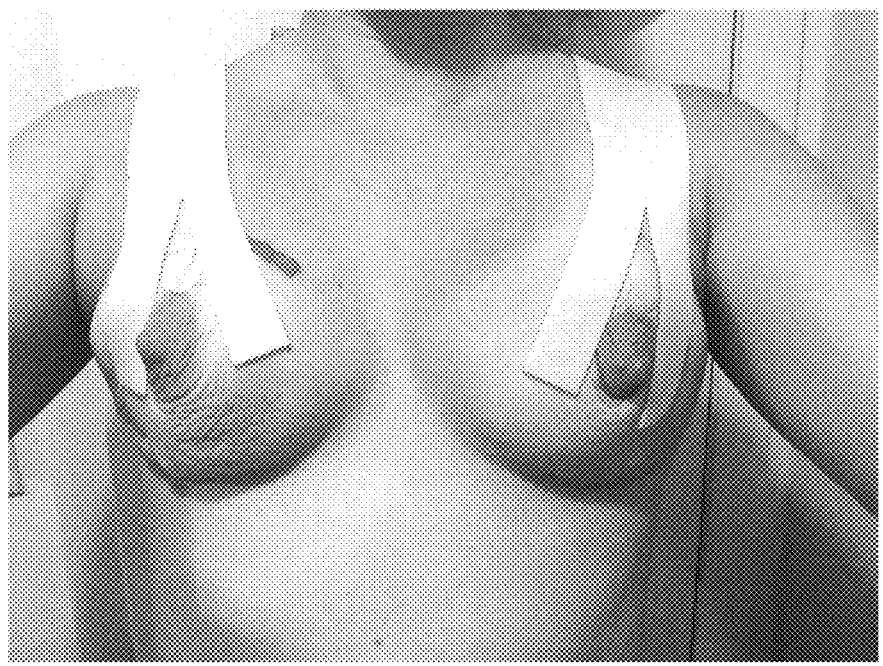
FIG. 7B depicts a hydrocolloid bra with an inverted V-design used during tissue expansion period for further manipulating the mastectomy skin flaps and NAC to a more ideal location.
Figure 7C:
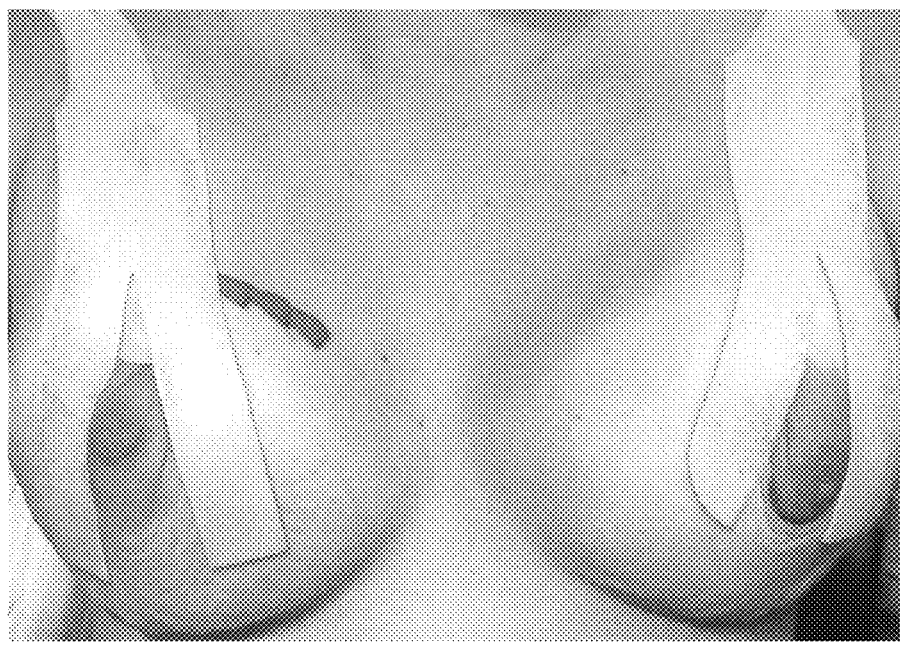
FIG. 7C depicts a hydrocolloid bra with an inverted and Y-design used during tissue expansion period for further manipulating the mastectomy skin flaps and NAC to a more ideal location. As in FIGS. 7B-7C, the current methodology can include a progressive manipulation with continuous use of V- and Y-shaped bra designs using the tissue plasticity and continued movement of mastectomy skin over the pectoralis major muscle.
Figure 7D:
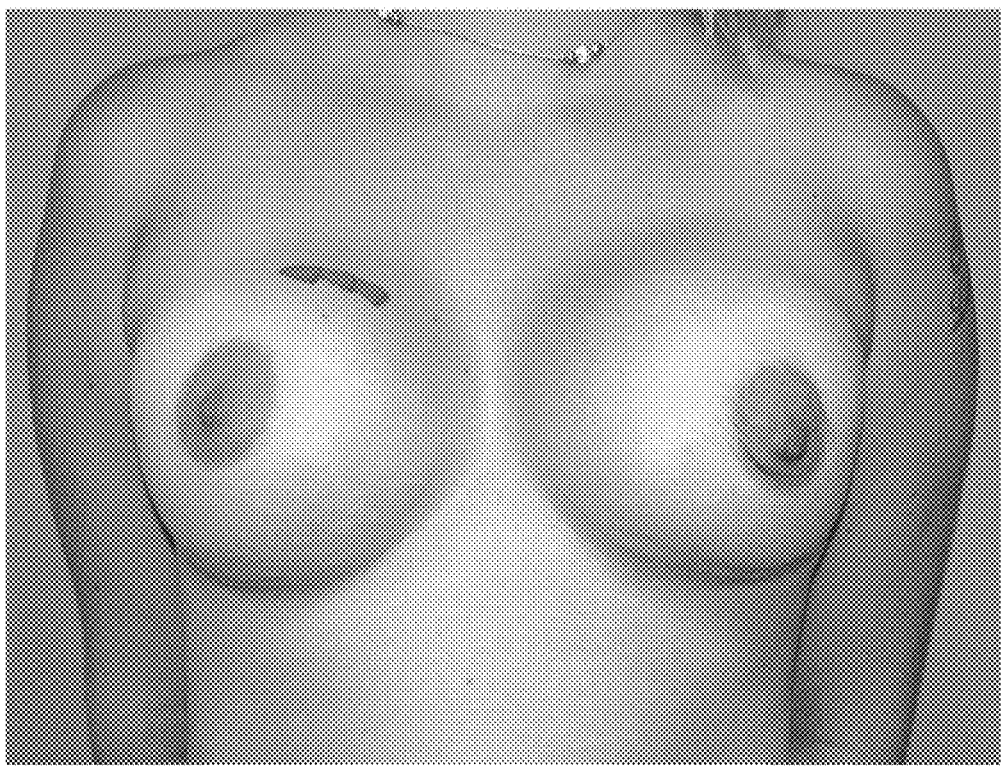
FIG. 7D is a post-operative photograph of a patient after bilateral NSM and use of hydrocolloid dressings, according to certain embodiments of the current invention.

FIGS. 5A-5D and 6A-6D depict the progression of two (2) patients using the foregoing methodology. FIGS. 5A and 6A depict the patients pre-operation; FIGS. 5B and 6B depict the patients with the hydrocolloid dressing applied after bilateral NSM; FIGS. 5C and 6C depict the patients with tissue expanders fully expanded; and FIGS. 5D and 6D depict the patients with permanent implants having replaced the tissue expanders.

Patients can be checked weekly for their nipple positioning in the period leading up the first expansion, and then at each expansion visit. If there are changes in skin folds or nipple positioning, then the mastectomy skin can gently be manipulated to a higher position with different designs of the hydrocolloid dressing. These designs include and can be referred to as the "inverted V design" and the "inverted Y design", where progression of the breasts using both designs can be seen in FIGS. 7A-7D. An inverted V/Y, or two separate strips of the hydrocolloid dressing, are cut for each breast that needs more precise positioning. The strips are placed onto the skin to put traction on it as it heals and fully adheres to underlying tissue. The strips are usually placed on either side of the nipple and can be manipulated by the physician as needed.

Figure 8A:
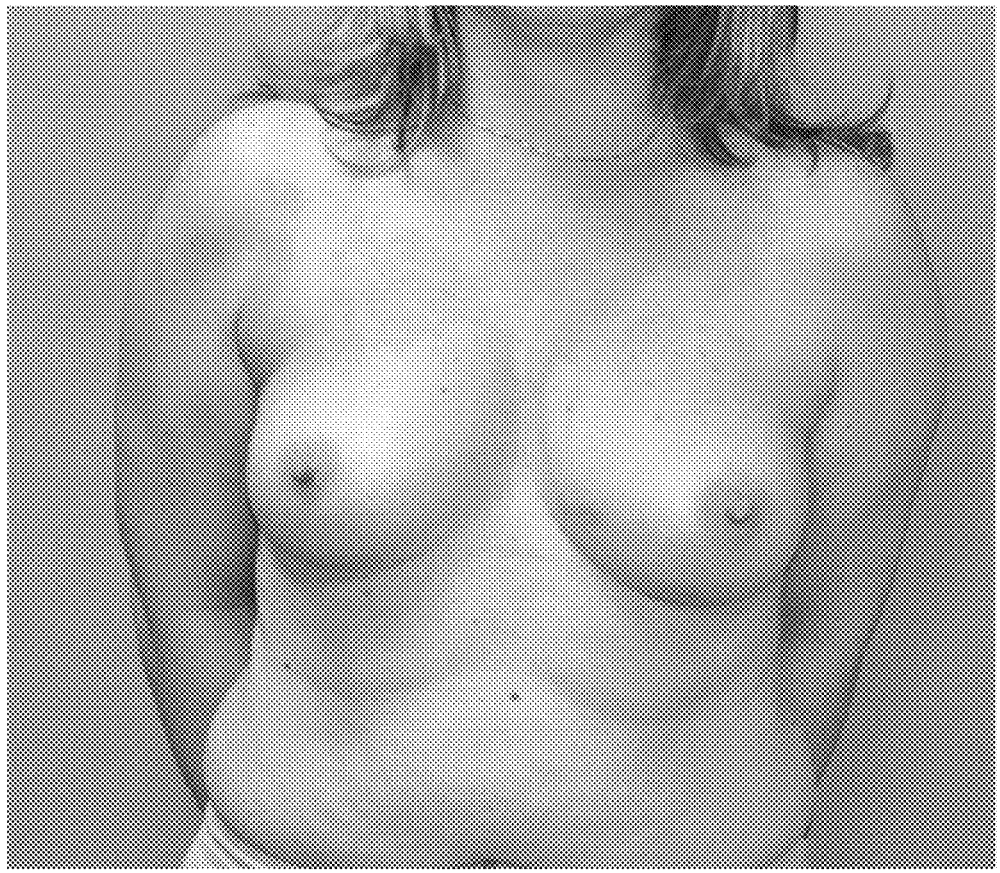
FIG. 8A is a pre-operative photograph of a patient before bilateral NSM.
Figure 8B:
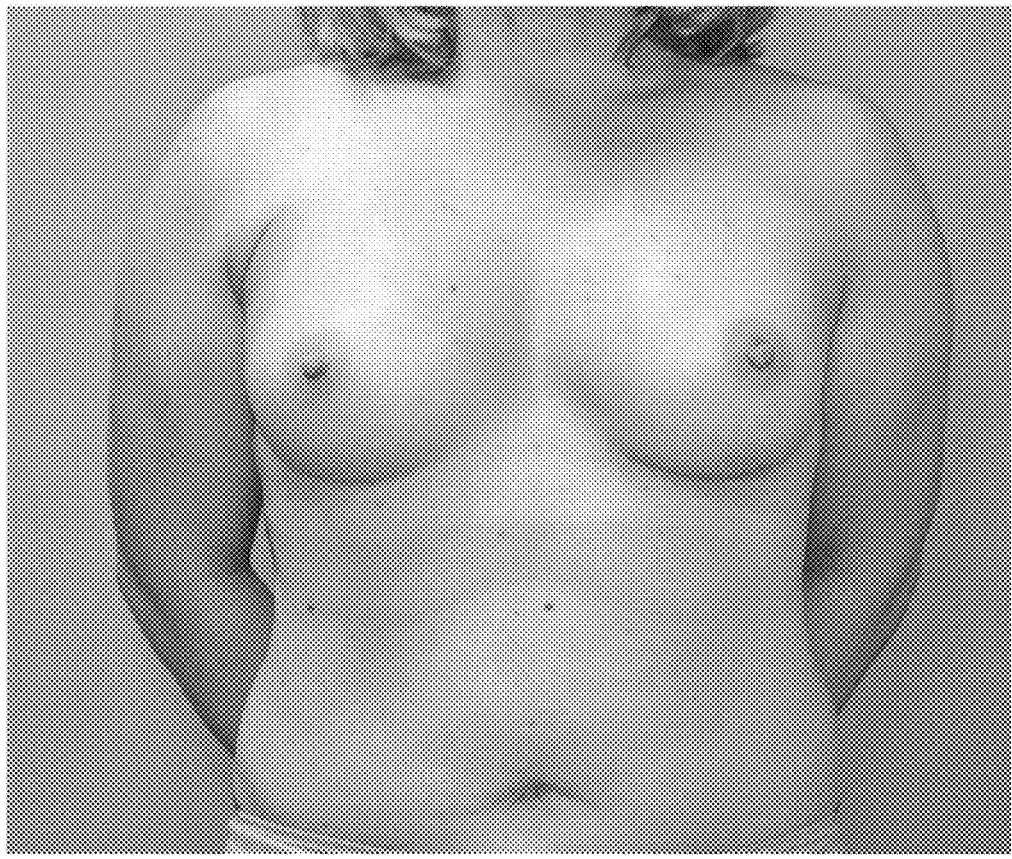
FIG. 8B is post-operative photograph of a patient after bilateral NSM and use of the hydrocolloid bra contemplated by the current invention.
Figure 9A:
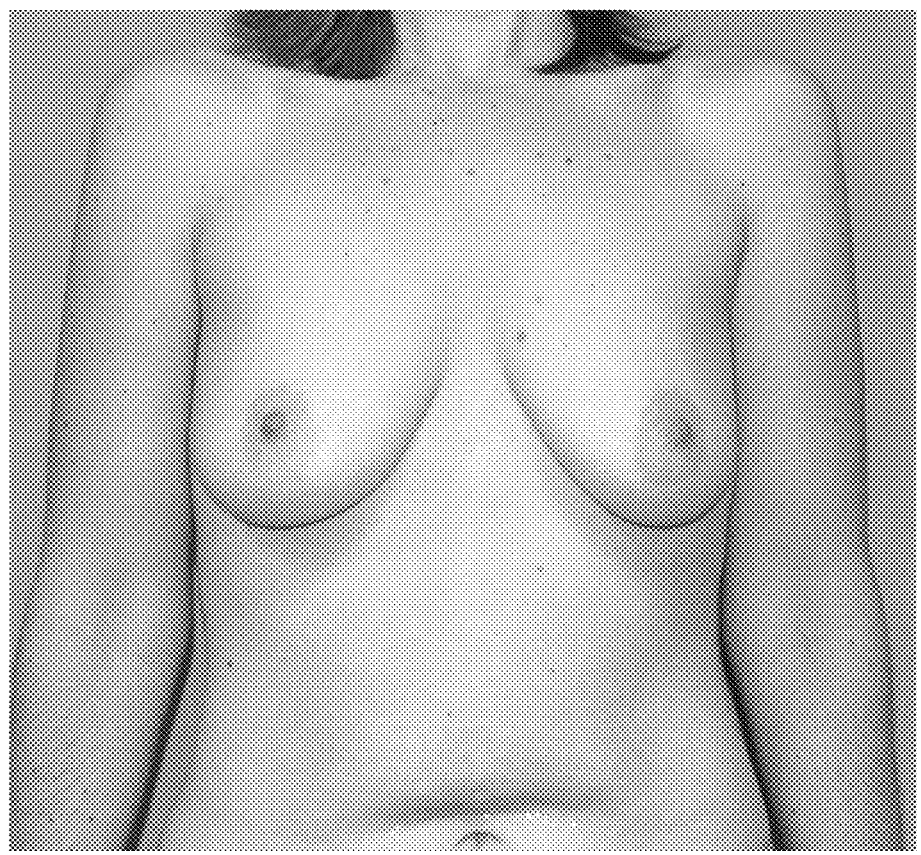
FIG. 9A is a pre-operative frontal photograph of a patient before bilateral NSM.
Figure 9B:
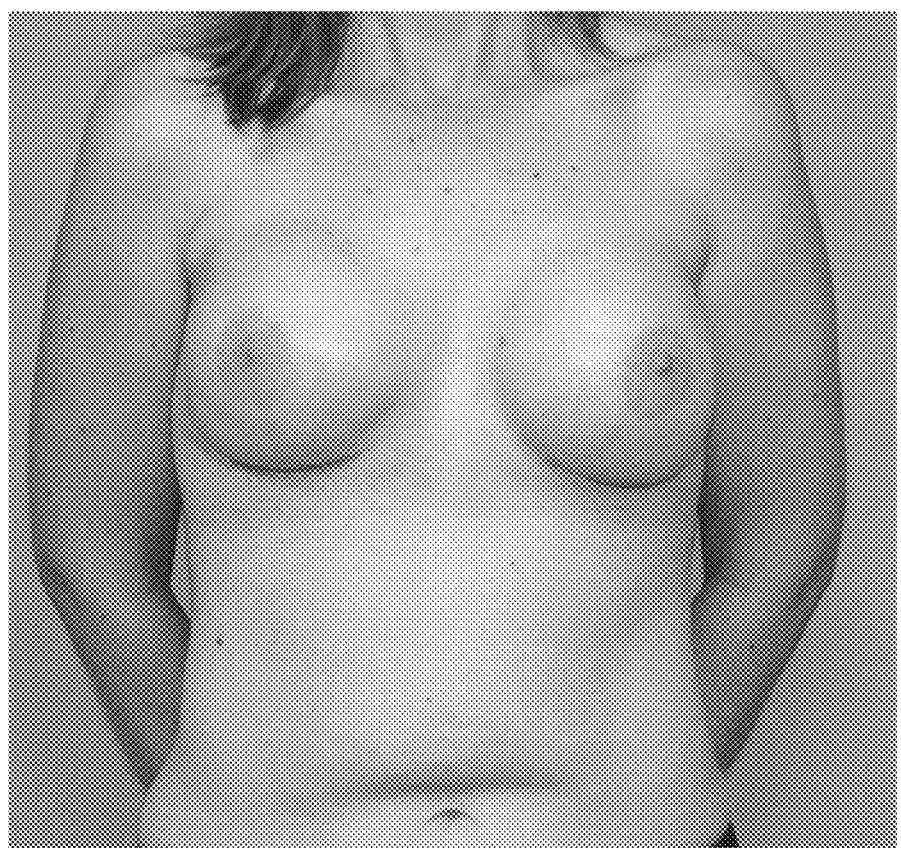
FIG. 9B is post-operative frontal photograph of a patient after bilateral NSM and use of the hydrocolloid bra contemplated by the current invention.
Figure 9C:
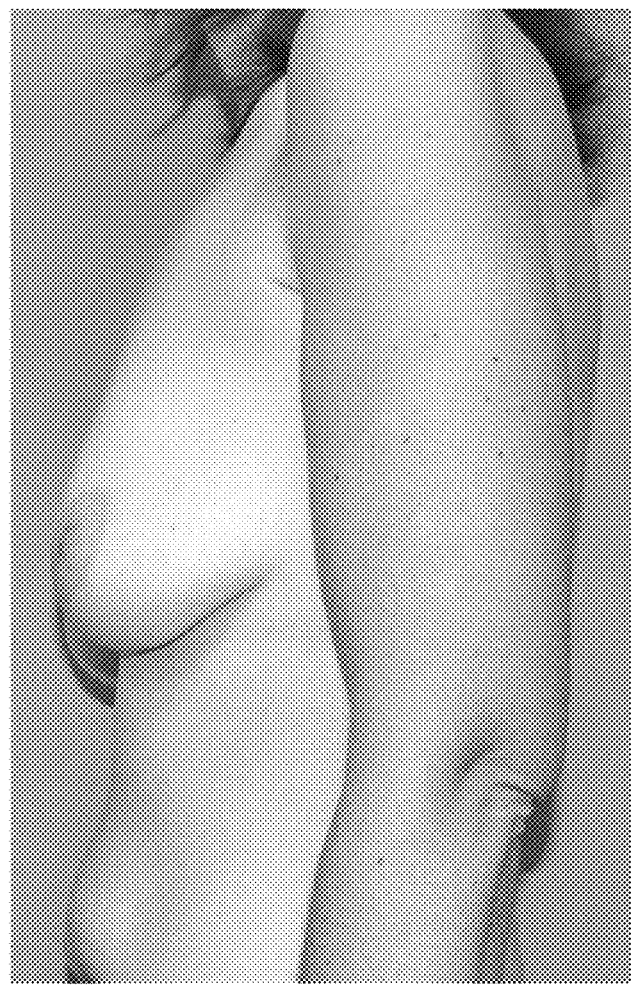
FIG. 9C is a pre-operative lateral photograph of the patient of FIG. 9A.
Figure 9D:
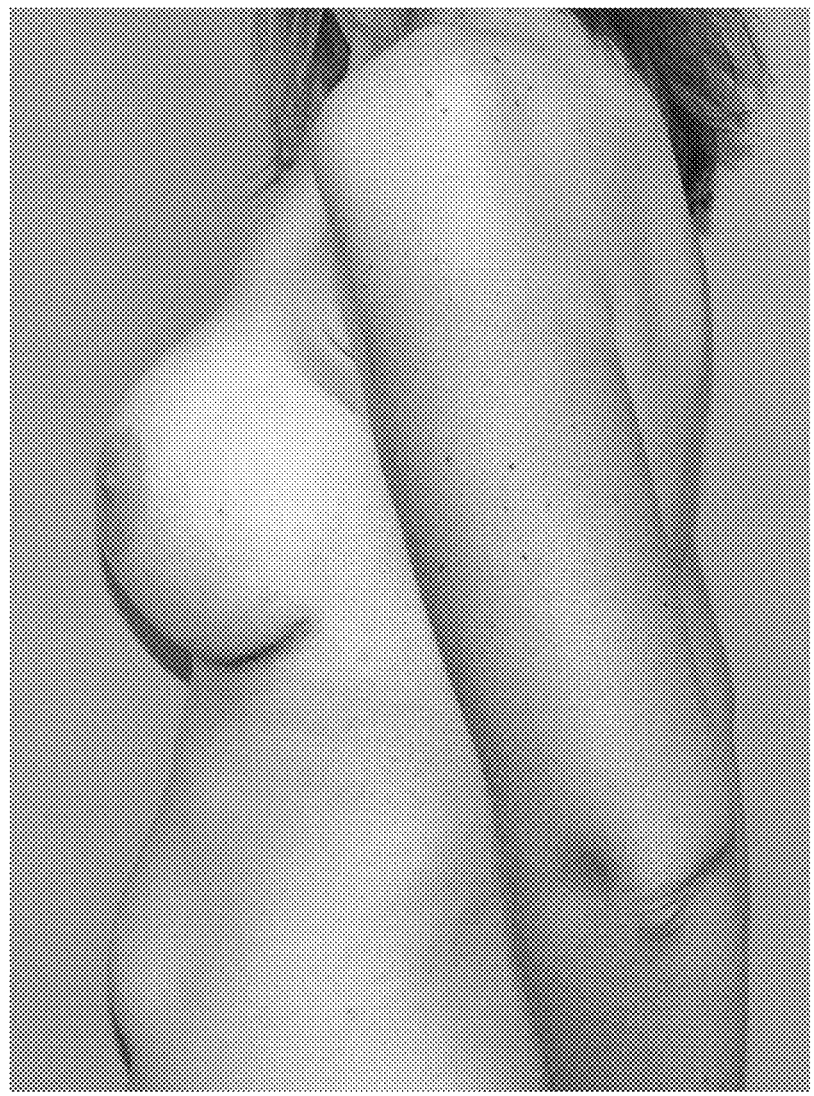
FIG. 9D is post-operative lateral photograph of the patient of FIG. 9B.

The expansion process is typically initiated approximately one month after surgery and continues weekly until the desired volume is achieved. During this time, the mastectomy skin and orientation of nipples are routinely checked because they can shift with expansion. Symmetry of the NAC and precise positioning of skin flaps is possible throughout the expansion period because of tissue plasticity. The NAC and skin flap positioning can thus benefit from additional skin dressing with the inverted-Y design. FIGS. 8A-8B depict a "before-and-after" progression of a patient where the inverted-Y design was used.

Approximately six (6) weeks after the final expansion, the expanders are exchanged to permanent implants in a conventional manner. Grade 2 ptosis can be improved with this technique (see mechanism of FIG. 1C and FIGS. 9A-9D where ptosis is improved by elevating the NAC).

Statistical Analysis

Descriptive statistics were used to summarize patient characteristics for compared groups. Differences in categorical variables as per compared groups were assessed using the chi-square test and summarized as odds ratios (OR) along with 95% confidence intervals (CI). Differences in continuous variables was assessed using independent samples T-test and summarized as mean difference (MD) along with 95% CI. Type I error for all comparisons was set at 5%. Bonferroni corrections were applied to adjust for multiple comparisons. All data analyses were performed using SPSS statistical analysis software.

Results

Photographs of pre-operative and post-operative patients can be seen in FIGS. 5A-5D, 6A-6D, 7A-7D, 8A-8B, and 9A-9D. These images show successful results of use of the hydrocolloid dressing, specifically precise positioning of the nipples without ischemia or other complications.

Specifically, of the 35 patient breasts treated with the hydrocolloid dressing, average age at time of surgery was about 47 years, average mastectomy specimen weight was about 409 g, average tumor margin was about 0.6 cm, average expander size was about 495 mL, average fill time (from mastectomy to final tissue expander fill) was about 14 weeks, and average final fill volume was about 606 mL. Of the 28 patient breasts treated using conventional methods and no hydrocolloid dressing, the average age at time of surgery was about 49 years, average mastectomy specimen weight was about 400 g, average tumor margin was about 0.9 cm, average expander size was about 466 mL, average fill time was about 16 weeks, and average final fill volume was about 606 mL. See Table 1.

TABLE 1

Patient characteristics.

| Hydrocolloid_bra | | Breast Weight (R/L) Grams | Tissue Expander Size (mL) | Age at Operation | Pre-Op Nipple to IMF (R./L) | Tumor Size (cm) |
|---|---|---|---|---|---|---|
| Hydrocolloid bra | N | 35 | 31 | 35 | 35 | 35 |
| | Median | 374.000 | 500.000 | 48.000 | 8.000 | .000 |
| | Mean | 408.900 | 495.161 | 46.914 | 7.486 | .6623 |
| | Minimum | 178.0 | 400.0 | 30.0 | 3.0 | .00 |
| | Maximum | 865.0 | 700.0 | 64.0 | 11.0 | 3.00 |
| No-Hydrocolloid bra | N | 28 | 21 | 28 | 28 | 28 |
| | Median | 343.000 | 400.000 | 52.000 | 8.000 | .000 |
| | Mean | 400.000 | 466.667 | 49.250 | 7.411 | .9179 |
| | Minimum | 150.0 | 400.0 | 27.0 | 5.0 | .00 |
| | Maximum | 1064.0 | 650.0 | 66.0 | 10.0 | 8.00 |
| Total | N | 63 | 52 | 63 | 63 | 63 |
| | Median | 353.000 | 500.000 | 48.000 | 8.000 | .000 |
| | Mean | 404.944 | 483.654 | 47.952 | 7.452 | .7759 |
| | Minimum | 150.0 | 400.0 | 27.0 | 3.0 | .00 |
| | Maximum | 1064.0 | 700.0 | 66.0 | 11.0 | 8.00 |

Optimum nipple positioning was significantly higher with the test group compared to the control group (OR 50.0; 95% CI 10.9 to 230.1; p<0.0001). Specifically, optimum nipple position occurred in the control group for 3 of 28 cases (10.7%) and in the test group for 30 of 35 cases (85.7%). See Table 2.

TABLE 2

Nipple position was significantly better with the test group.

| | | | Hydrocolloid_bra | | |
|---|---|---|---|---|---|
| | | | Hydrocolloid bra | No-Hydrocolloid bra | Total |
| Nipple position code | Correct | Count | 30a | 3b | 33 |
| | | % within nipple position code | 90.9% | 9.1% | 100.0% |
| | | % within Hydrocolloid_bra | 85.7% | 10.7% | 52.4% |
| | | % of total | 47.6% | 4.8% | 52.4% |
| | Incorrect | Count | 5a | 25b | 30 |
| | | % within nipple position code | 16.7% | 83.3% | 100.0% |
| | | % within Hydrocolloid_bra | 14.3% | 89.3% | 47.6% |
| | | % of total | 7.9% | 39.7% | 47.6% |
| | Total | Count | 35 | 28 | 63 |
| | | % within nipple position code | 55.6% | 44.4% | 100.0% |
| | | % within Hydrocolloid_bra | 100.0% | 100.0% | 100.0% |
| | | % of total | 55.6% | 44.4% | 100.0% |

TABLE 2-continued

Nipple position was significantly better with the test group.

|  | Value | 95% Confidence Interval | |
|---|---|---|---|
|  |  | Lower | Upper |
| Odds ratio for nipple position code (correct/incorrect) | 50.000 | 10.864 | 230.123 |
| N for valid cases | 63 | | |

Complications were higher in the control group compared with the test group (OR 4.5; 95% CI 1.35 to 15.04; p=0.021). Specifically, complications occurred in the control group for 12 of 28 cases (42.9%) and in the test group for 5 of 35 cases (14.3%). See Table 3.

TABLE 3

Complications were significantly less in the test group.

| | | | Complication | | |
|---|---|---|---|---|---|
| | | | No | Yes | Total |
| Hydro-colloid_bra | Hydro-colloid bra | Count | 30a | 5b | 35 |
| | | % within Hydrocolliod_bra | 85.7% | 14.3% | 100.0% |
| | | % within complication | 65.2% | 29.4% | 55.6% |
| | | % of total | 47.6% | 7.9% | 55.6% |
| | No-Hydro-colloid bra | Count | 16a | 12b | 28 |
| | | % within Hydrocolloid_bra | 57.1% | 42.9% | 100.0% |
| | | % within complication | 34.8% | 70.6% | 44.4% |
| | | % of total | 25.4% | 19.0% | 44.4% |
| Total | | Count | 46 | 17 | 63 |
| | | % within Hydrocolloid_bra | 73.0% | 27.0% | 100.0% |
| | | % within complication | 100.0% | 100.0% | 100.0% |
| | | % of total | 73.0% | 27.0% | 100.0% |

| | Value | 95% Confidence Interval | |
|---|---|---|---|
| | | Lower | Upper |
| Odds ratio for Hydrocolloid_bra (Hydrocolloid bra/No-Hydrocolloid bra) | 4.500 | 1.346 | 15.044 |
| For cohort complication code = No | 1.500 | 1.059 | 2.125 |
| For cohort complication code = Yes | .333 | .133 | .834 |
| N for valid cases | 63 | | |

As was seen, the odds of complications were 4.5 times higher in the control group compared with test group (OR 4.5; 95% CI 1.35 to 15.04; p=0.021). The odds of optimum nipple positioning were 50 times higher in the test group compared with the control group (OR 50.0; 95% CI 10.9 to 230.1; p<0.0001). There was no difference in timing from mastectomy to end of expansion in the test group compared with the control group (MD −2.35; 95% CI −10.37 to 5.68). See Table 4.

TABLE 4

Fill time did not significantly increase in the test group.

| | Hydrocolloid_bra | N | Mean | Std. Deviation | Std. Error Mean |
|---|---|---|---|---|---|
| Fill_Time | Hydrocolloid bra | 35 | 13.87346939 | 9.498390047 | 1.605520952 |
| | No-Hydrocolloid bra | 28 | 16.21938776 | 21.25981103 | 4.017726635 |

| | | t-test for Equality of Means | | | |
|---|---|---|---|---|---|
| | | Sig. (2-tailed) | Mean Difference | Std. Error Difference | 95% Confidence Interval of the Lower |
| Fill_Time | Equal variances assumed | .561 | −2.34591837 | 4.011665875 | −10.3677401 |
| | Equal variances not assumed | .591 | −2.34591837 | 4.326641289 | −11.1242570 |

There was no significant difference between the groups in regards to age, breast weight, cancerous tumor size, tissue expander size, fill time, or final fill volume. Use of the hydrocolloid dressing did not hinder the surgeon in regards to cancer excision or expander size chosen. Use of the hydrocolloid dressing did not lengthen the time period in which the patient's expanders were being filled, and it did not affect the capacity of the breast tissue to expand to the average final fill volume similar to that of the control group. There was no difference in timing from mastectomy to completion of expansion in the test group compared to the control group (MD −2.35; 95% CI −10.37 to 5.68).

In summary, use of the hydrocolloid dressing, according to certain embodiments of the current invention, without intra-operative tissue expansion in NSM, achieved unexpected and highly successful results, as the hydrocolloid dressing decreased the odds of NAC necrosis and epidermolysis by 78% (OR 4.5; 95% CI 1.35 to 15.04; p=0.021), increased the odds of optimum nipple positioning by 98% (OR 50.0; 95% CI 10.9 to 230.1; p<0.0001) with less ptosis and greater elevation, decreased flap and NAC necrosis complications, did not statistically affect the length of time needed from mastectomy to final tissue expander fill (fill time) (i.e., total reconstructive time period in NSM patients did not increase), and did not affect the final fill volume capacity. The 98% success rate of optimum nipple positioning clearly was unexpected; though certain benefits were expected, it was not expected that the methodology and hydrocolloid dressing would result in this extraordinary, nearly perfect success.

Use of the hydrocolloid dressing paired with no intraoperative tissue expansion in NSM was seen to be a highly successful technique overcoming many of the problems seen in the conventional art. Use of the hydrocolloid dressing improves nipple positioning by allowing the NAC to be placed precisely in the ideal location without allowing loose, redundant breast skin to determine its location. The hydrocolloid dressing decreases complications by applying a wound healing environment to traumatized mastectomy skin. By eliminating intraoperative fill use of ADM, the limits of the mastectomy skin are not pushed in the most critical immediate post-operative period. Even without intraoperative fill and starting the expansions within a month, the hydrocolloid dressing does not increase total reconstructive time period in NSM candidates. By using the current technique with hydrocolloid dressings, NSM can be safely performed since ADM complications and tissue tension factors are eliminated by total sub-pectoral coverage and no initial tissue expander fill.

With the current technique using the hydrocolloid dressing, after a NSM the new position of the NAC can be determined by the hydrocolloid dressing in a high set and by re-draping the mastectomy skin in a superior location. Therefore, the ptotic look of the original breast is converted to a more youthful or otherwise desirable looking breast. It was observed that decreased ptosis is appreciated by most patients and is expected as a positive outcome of their breast cancer journey. By post-operative photographic assessment, this study showed improvement of ptosis and improvement of new nipple position compared to pre-operative location in the patients who used the hydrocolloid dressing.

Although data is insufficient regarding ADM use for NSM, data exists to support their use for direct implant placement after NSM. For consistent results, the current technique was seen to be reliable without the increased risks associated with direct implant placement method. By creating a moist healing environment and absorbing exudate, hydrocolloid dressings have many advantages. These include faster healing, non-adhesive wound dressing, reduced wound pain, and reduced frequency of dressing changes. The use of hydrocolloid dressings after NSM with no ADM and no intraoperative fill is an efficient and extremely effective method for achieving precise nipple placement, while also consistently protecting the viability of the overlying tissue.

Glossary of Claim Terms

Afflicted breast mound: This term is used herein to refer to the body of a breast that underwent a nipple-sparing mastectomy.

Desired post-NSM/SSM nipple position: This term is used herein to refer to an optimal position of the nipple and/or nipple-areolar complex after a nipple- or skin-sparing mastectomy is performed on the underlying breast. The term "optimal" can mean a position that is desired by the patient or surgeon (e.g., an aesthetically pleasing position, a position that is symmetrical to the other breast, etc.)

Fully extended hydrocolloid dressing: This term is used herein to refer to the lack of creases in a hydrocolloid dressing after application to the breast.

Hydrocolloid dressing: This term is used herein to refer to a covering formed of a material that forms a colloid when admixed with water.

Inferior: This term is used herein to refer to a relative position of an object or component being lower along a length of the patient (i.e., further away from the patient's head).

Mirror image: This term is used herein to refer to two apparatuses that substantially reflect each other in a lateral (left-to-right) direction, as if seen in a mirror.

Patient: This term is interchangeable with the terms "subject" or "organism" is used herein to include humans and mammals (e.g., mice, rats, pigs, cats, dogs, and horses). Typical hosts to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

Superior: This term is used herein to refer to a relative position of an object or component being higher along a length of the patient (i.e., closer to the patient's head).

Symmetrical: This term is used herein to refer to two apparatuses that have a proportionate arrangement of components with corresponding relationships to each other.

Wound healing environment: This term is used herein to refer to a substantially enclosed setting in which the surgically-affected skin and tissue of a breast can heal without undesired external influences.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of elevating and positioning a nipple of a patient after a nipple-sparing mastectomy (NSM) or a skin-sparing mastectomy (SSM), comprising:
    providing a hydrocolloid dressing to be positioned over a breast of said patient, said hydrocolloid dressing having a main body and a strap extension;
    creating an aperture in said main body of said hydrocolloid dressing, said aperture corresponding to a desired post-NSM/SSM nipple position of said breast of said patient;
    securing said hydrocolloid dressing over said breast of said patient with said main body disposed over an afflicted breast mound of said patient, said strap extension extending toward or over a corresponding shoulder of said patient, and said nipple of said patient disposed within said aperture in said main body of said hydrocolloid dressing, wherein said hydrocolloid dressing is fully extended;
    allowing skin and tissue corresponding to said breast of said patient to heal within a wound healing environment created between said breast and said hydrocolloid dressing, thus also permitting said nipple of said patient to be positioned in said desired post-NSM/SSM position; and
    evaluating said nipple of said patient to determine whether said desired post-NSM/SSM position has been reached.

2. The method as in claim 1, wherein no acellular dermal matrix and no intraoperative fill is used after said nipple-sparing mastectomy.

3. The method as in claim 1, further comprising manipulating said skin of said breast superiorly resulting from changes in skin folds or nipple positioning.

4. The method as in claim 3, further comprising:
    as a result of said evaluation of said nipple being that said nipple is not in said desired post-NSM/SSM position, removing said hydrocolloid dressing from said patient;
    providing a second hydrocolloid dressing to be positioned on said breast of said patient, said second hydrocolloid dressing having a shoulder component and two (2) branched extensions extending inferiorly from said shoulder component;
    securing said second hydrocolloid dressing over said breast of said patient with a first extension of said two (2) branched extensions disposed on one lateral side of said nipple, a second extension of said two (2) branched extensions disposed on an opposite lateral side of said nipple, and said shoulder component disposed on said corresponding shoulder of said patient, wherein said second hydrocolloid dressing is fully extended; and
    allowing said skin and tissue corresponding to said breast of said patient to position said nipple of said patient in said desired post-NSM/SSM position.

5. The method as in claim 1, wherein said nipple-sparing mastectomy is a bilateral nipple-sparing mastectomy and said hydrocolloid dressing is a first hydrocolloid dressing, said method further comprising:
    providing a second hydrocolloid dressing to be positioned over an opposing breast of said patient, said second hydrocolloid dressing having a main body and a strap extension, said second hydrocolloid dressing being a mirror image of said first hydrocolloid dressing, said second hydrocolloid dressing being symmetrical to said first hydrocolloid dressing;
    creating an aperture in said main body of said second hydrocolloid dressing, said aperture corresponding to a desired post-NSM/SSM nipple position of said opposing breast of said patient, wherein said aperture of said second hydrocolloid dressing is aligned with said aperture of said first hydrocolloid dressing, such that said desired post-NSM/SSM nipple positions are symmetrical on said patient;
    securing said second hydrocolloid dressing over said opposing breast of said patient with said main body disposed over an afflicted opposing breast mound of said patient, said strap extension extending toward or over a corresponding opposing shoulder of said patient, and an opposing nipple of said patient disposed within said aperture in said main body of said second hydrocolloid dressing, wherein said second hydrocolloid dressing is fully extended;
    allowing said skin and tissue corresponding to said opposing breast of said patient to heal within a wound healing environment created between said opposing breast and said second hydrocolloid dressing, thus also permitting said opposing nipple of said patient to be positioned in said desired post-NSM/SSM position; and
    evaluating said opposing nipple of said patient to determine whether said desired post-NSM/SSM position has been reached.

6. The method as in claim 5, further comprising manipulating said skin of said breast and said opposing breast superiorly resulting from changes in skin folds or nipple positioning.

7. The method as in claim 6, further comprising:
    as a result of said evaluation of said nipple being that said nipple is not in said desired post-NSM/SSM position, removing said hydrocolloid dressing from said patient;
    providing a third hydrocolloid dressing to be positioned on said breast of said patient, said third hydrocolloid dressing having a shoulder component and two (2) branched extensions extending inferiorly from said shoulder component;
    securing said third hydrocolloid dressing over said breast of said patient with a first extension of said two (2) branched extensions disposed on one lateral side of said nipple, a third extension of said two (2) branched extensions disposed on an opposite lateral side of said nipple, and said shoulder component disposed on said corresponding shoulder of said patient, wherein said third hydrocolloid dressing is fully extended;
    allowing said skin and tissue corresponding to said breast of said patient to position said nipple of said patient in said desired post-NSM/SSM position;
    as a result of said evaluation of said opposing nipple being that said opposing nipple is not in said desired post-NSM/SSM position, removing said second hydrocolloid dressing from said patient;
    providing a fourth hydrocolloid dressing to be positioned on said opposing breast of said patient, said fourth hydrocolloid dressing having a shoulder component and two (2) branched extensions extending inferiorly from said shoulder component;

securing said fourth hydrocolloid dressing over said opposing breast of said patient with a first extension of said two (2) branched extensions disposed on one lateral side of said opposing nipple, a second extension of said two (2) branched extensions disposed on an opposite lateral side of said opposing nipple, and said shoulder component disposed on said corresponding opposing shoulder of said patient, wherein said fourth hydrocolloid dressing is fully extended; and allowing said skin and tissue corresponding to said opposing breast of said patient to position said opposing nipple of said patient in said desired post-NSM/SSM position.

8. The method as in claim 1, wherein the step of positioning said nipple of said patient within said aperture in said main body of said hydrocolloid dressing is performed by pulling and draping redundant mastectomy skin with said nipple superiorly toward said corresponding shoulder of said patient until said nipple is disposed within said aperture.

9. The method as in claim 1, wherein an incision site formed during said nipple sparing mastectomy is left uncovered when securing said hydrocolloid dressing over said breast of said patient.

10. The method as in claim 1, wherein the step of securing said hydrocolloid dressing over said breast of said patient is performed by adhering an inferior edge of said hydrocolloid dressing and continuing to adhere said hydrocolloid dressing to said breast in a superior direction until said strap extension is adhered to said corresponding shoulder of said patient.

11. A method of elevating and positioning a nipple of a patient after a bilateral nipple-sparing mastectomy (NSM) without use of acellular dermal matrix or intraoperative fill after said nipple-sparing mastectomy, said method comprising:

providing a first hydrocolloid dressing to be positioned over a breast of said patient, said first hydrocolloid dressing having a main body and a strap extension;

providing a second hydrocolloid dressing to be positioned over an opposing breast of said patient, said second hydrocolloid dressing having a main body and a strap extension, said second hydrocolloid dressing being a mirror image of said first hydrocolloid dressing, said second hydrocolloid dressing being symmetrical to said first hydrocolloid dressing;

creating an aperture in said main body of said first hydrocolloid dressing, said aperture corresponding to a desired post-NSM/SSM nipple position of said breast of said patient;

creating an aperture in said main body of said second hydrocolloid dressing, said aperture corresponding to a desired post-NSM/SSM nipple position of said opposing breast of said patient, wherein said aperture of said second hydrocolloid dressing is aligned with said aperture of said first hydrocolloid dressing, such that said desired post-NSM/SSM nipple positions are symmetrical on said patient;

securing said first hydrocolloid dressing over said breast of said patient with said main body disposed over an afflicted breast mound of said patient, said strap extension extending toward or over a corresponding shoulder of said patient, and said nipple of said patient disposed within said aperture in said main body of said first hydrocolloid dressing, wherein said first hydrocolloid dressing is fully extended, wherein the step of positioning said nipple of said patient within said aperture in said main body of said first hydrocolloid dressing is performed by pulling and draping redundant mastectomy skin with said nipple superiorly toward said corresponding shoulder of said patient until said nipple is disposed within said aperture, wherein an incision site formed during said nipple-sparing mastectomy is left uncovered when securing said first hydrocolloid dressing over said breast of said patient, wherein the step of securing said first hydrocolloid dressing over said breast of said patient is performed by adhering an inferior edge of said first hydrocolloid dressing and continuing to adhere said first hydrocolloid dressing to said breast in a superior direction until said strap extension is adhered to said corresponding shoulder of said patient;

securing said second hydrocolloid dressing over said opposing breast of said patient with said main body disposed over an afflicted opposing breast mound of said patient, said strap extension extending toward or over a corresponding opposing shoulder of said patient, and an opposing nipple of said patient disposed within said aperture in said main body of said second hydrocolloid dressing, wherein said second hydrocolloid dressing is fully extended, wherein the step of positioning said opposing nipple of said patient within said aperture in said main body of said second hydrocolloid dressing is performed by pulling and draping redundant mastectomy skin with said opposing nipple superiorly toward said corresponding opposing shoulder of said patient until said opposing nipple is disposed within said aperture, wherein an incision site formed during said nipple-sparing mastectomy is left uncovered when securing said second hydrocolloid dressing over said breast of said patient, wherein the step of securing said second hydrocolloid dressing over said opposing breast of said patient is performed by adhering an inferior edge of said second hydrocolloid dressing and continuing to adhere said second hydrocolloid dressing to said opposing breast in a superior direction until said strap extension is adhered to said corresponding opposing shoulder of said patient;

allowing skin and tissue corresponding to said breast and said opposing breast of said patient to heal within a wound healing environment created between said breast and said first and second hydrocolloid dressings, thus also permitting said nipple and said opposing nipple of said patient to be positioned in said desired post-NSM/SSM positions;

evaluating said nipple and said opposing nipple of said patient to determine whether said desired post-NSM/SSM positions have been reached;

manipulating said skin of said breast and said opposing breast superiorly resulting from changes in skin folds or nipple positioning;

as a result of said evaluation of said nipple and said opposing nipple being that said nipple and said opposing nipple are not in said desired post-NSM/SSM positions, removing said first and second hydrocolloid dressings from said patient;

providing a third hydrocolloid dressing to be positioned on said breast of said patient, said third hydrocolloid dressing having a shoulder component and two (2) branched extensions extending inferiorly from said shoulder component;
providing a fourth hydrocolloid dressing to be positioned on said opposing breast of said patient, said fourth hydrocolloid dressing having a shoulder component and two (2) branched extensions extending inferiorly from said shoulder component;
securing said third hydrocolloid dressing over said breast of said patient with a first extension of said two (2) branched extensions disposed on one lateral side of said nipple, a third extension of said two (2) branched extensions disposed on an opposite lateral side of said nipple, and said shoulder component disposed on said corresponding shoulder of said patient, wherein said third hydrocolloid dressing is fully extended;
securing said fourth hydrocolloid dressing over said opposing breast of said patient with a first extension of said two (2) branched extensions disposed on one lateral side of said opposing nipple, a second extension of said two (2) branched extensions disposed on an opposite lateral side of said opposing nipple, and said shoulder component disposed on said corresponding opposing shoulder of said patient, wherein said fourth hydrocolloid dressing is fully extended; and
allowing said skin and tissue corresponding to said breast and said opposing breast of said patient to position said nipple and said opposing nipple of said patient in said desired post-NSM/SSM positions.

12. A method, comprising:
performing a bilateral nipple-sparing mastectomy (NSM) without use of acellular dermal matrix or intraoperative fill;
providing a first hydrocolloid dressing to be positioned over a breast of said patient, said first hydrocolloid dressing having a main body and a strap extension;
providing a second hydrocolloid dressing to be positioned over an opposing breast of said patient, said second hydrocolloid dressing having a main body and a strap extension, said second hydrocolloid dressing being a mirror image of said first hydrocolloid dressing, said second hydrocolloid dressing being symmetrical to said first hydrocolloid dressing;
creating an aperture in said main body of said first hydrocolloid dressing, said aperture corresponding to a desired post-NSM/SSM nipple position of said breast of said patient;
creating an aperture in said main body of said second hydrocolloid dressing, said aperture corresponding to a desired post-NSM/SSM nipple position of said opposing breast of said patient, wherein said aperture of said second hydrocolloid dressing is aligned with said aperture of said first hydrocolloid dressing, such that said desired post-NSM/SSM nipple positions are symmetrical on said patient;
securing said first hydrocolloid dressing over said breast of said patient with said main body disposed over an afflicted breast mound of said patient, said strap extension extending toward or over a corresponding shoulder of said patient, and said nipple of said patient disposed within said aperture in said main body of said first hydrocolloid dressing, wherein said first hydrocolloid dressing is fully extended,
wherein the step of positioning said nipple of said patient within said aperture in said main body of said first hydrocolloid dressing is performed by pulling and draping redundant mastectomy skin with said nipple superiorly toward said corresponding shoulder of said patient until said nipple is disposed within said aperture,
wherein an incision site formed during said nipple-sparing mastectomy is left uncovered when securing said first hydrocolloid dressing over said breast of said patient,
wherein the step of securing said first hydrocolloid dressing over said breast of said patient is performed by adhering an inferior edge of said first hydrocolloid dressing and continuing to adhere said first hydrocolloid dressing to said breast in a superior direction until said strap extension is adhered to said corresponding shoulder of said patient;
securing said second hydrocolloid dressing over said opposing breast of said patient with said main body disposed over an afflicted opposing breast mound of said patient, said strap extension extending toward or over a corresponding opposing shoulder of said patient, and an opposing nipple of said patient disposed within said aperture in said main body of said second hydrocolloid dressing, wherein said second hydrocolloid dressing is fully extended,
wherein the step of positioning said opposing nipple of said patient within said aperture in said main body of said second hydrocolloid dressing is performed by pulling and draping redundant mastectomy skin with said opposing nipple superiorly toward said corresponding opposing shoulder of said patient until said opposing nipple is disposed within said aperture,
wherein an incision site formed during said nipple-sparing mastectomy is left uncovered when securing said second hydrocolloid dressing over said breast of said patient,
wherein the step of securing said second hydrocolloid dressing over said opposing breast of said patient is performed by adhering an inferior edge of said second hydrocolloid dressing and continuing to adhere said second hydrocolloid dressing to said opposing breast in a superior direction until said strap extension is adhered to said corresponding opposing shoulder of said patient;
allowing skin and tissue corresponding to said breast and said opposing breast of said patient to heal within a wound healing environment created between said breast and said first and second hydrocolloid dressings, thus also permitting said nipple and said opposing nipple of said patient to be positioned in said desired post-NSM/SSM positions;
evaluating said nipple and said opposing nipple of said patient to determine whether said desired post-NSM/SSM positions have been reached.

13. The method as in claim 12, further comprising:
manipulating said skin of said breast and said opposing breast superiorly resulting from changes in skin folds or nipple positioning;
as a result of said evaluation of said nipple and said opposing nipple being that said nipple and said opposing nipple are not in said desired post-NSM/SSM positions, removing said first and second hydrocolloid dressings from said patient;
providing a third hydrocolloid dressing to be positioned on said breast of said patient, said third hydrocolloid dressing having a shoulder component and two (2) branched extensions extending inferiorly from said shoulder component;
providing a fourth hydrocolloid dressing to be positioned on said opposing breast of said patient, said fourth hydrocolloid dressing having a shoulder component and two (2) branched extensions extending inferiorly from said shoulder component;

securing said third hydrocolloid dressing over said breast of said patient with a first extension of said two (2) branched extensions disposed on one lateral side of said nipple, a third extension of said two (2) branched extensions disposed on an opposite lateral side of said nipple, and said shoulder component disposed on said corresponding shoulder of said patient, wherein said third hydrocolloid dressing is fully extended;

securing said fourth hydrocolloid dressing over said opposing breast of said patient with a first extension of said two (2) branched extensions disposed on one lateral side of said opposing nipple, a second extension of said two (2) branched extensions disposed on an opposite lateral side of said opposing nipple, and said shoulder component disposed on said corresponding opposing shoulder of said patient, wherein said fourth hydrocolloid dressing is fully extended; and allowing said skin and tissue corresponding to said breast and said opposing breast of said patient to position said nipple and said opposing nipple of said patient in said desired post-NSM/SSM positions.

* * * * *